US012601740B2

(12) United States Patent (10) Patent No.: US 12,601,740 B2
    Cox et al.                                        (45) Date of Patent:      Apr. 14, 2026

(54) METHOD AND KIT FOR IDENTIFYING ANTIMICROBIAL AGENTS AND EFFECTIVE CONCENTRATIONS THEREOF

(71) Applicant: COBIO DIAGNOSTICS INC., Golden, CO (US)

(72) Inventors: Christopher R. Cox, Golden, CO (US); Andrew J. Logan, Denver, CO (US)

(73) Assignee: COBIO DIAGNOSTICS INC., Golden, CO (US)

( * ) Notice: Subject to any disclaimer, the term of this patent is extended or adjusted under 35 U.S.C. 154(b) by 110 days.

(21) Appl. No.: 18/280,907

(22) PCT Filed: Mar. 8, 2022

(86) PCT No.: PCT/US2022/019280
    § 371 (c)(1),
    (2) Date: Sep. 7, 2023

(87) PCT Pub. No.: WO2022/192208
    PCT Pub. Date: Sep. 15, 2022

(65) Prior Publication Data
    US 2024/0151719 A1     May 9, 2024

Related U.S. Application Data

(60) Provisional application No. 63/158,061, filed on Mar. 8, 2021.

(51) Int. Cl.
    *G01N 33/569*        (2006.01)
    *G01N 33/58*         (2006.01)

(52) U.S. Cl.
    CPC . *G01N 33/56916* (2013.01); *G01N 33/56938* (2013.01); *G01N 33/58* (2013.01); *G01N 2333/22* (2013.01); *G01N 2333/26* (2013.01);

*G01N 2333/265* (2013.01); *G01N 2333/31* (2013.01); *G01N 2333/315* (2013.01)

(58) Field of Classification Search
    CPC ....... G01N 33/56916; G01N 33/56938; G01N 33/58; G01N 2333/22; G01N 2333/26; G01N 2333/265; G01N 2333/31; G01N 2333/315
    See application file for complete search history.

(56) References Cited

U.S. PATENT DOCUMENTS

| 2007/0178450 A1 | 8/2007 | Wheeler |
| 2015/0004595 A1 | 1/2015 | Koeris et al. |
| 2021/0062239 A1 | 3/2021 | Erickson et al. |

FOREIGN PATENT DOCUMENTS

| WO | 2005001475 A2 | 1/2005 |
| WO | 2017127684 A1 | 7/2017 |
| WO | 2019209982 A1 | 10/2019 |

OTHER PUBLICATIONS

European Search Report dated Feb. 10, 2025, for Europe Application No. 22767771.3, 9 oages.

*Primary Examiner* — Robert A Zeman

(57) ABSTRACT

A method and kit for for determining of an effective concentration of an antimicrobial agent for inhibiting bacterial growth are provided. The method and kit involve the use of a first and second multiwell receptacle. A fluid sample containing or suspected to contain one or more microbial organisms is dispensed into the wells of the first multiwell receptacle containing a range of dilutions of an antimicrobial agent, growth medium and a bacteriophage to form assay mixtures in the wells. The assay mixtures are then transferred to the corresponding wells of the second multiwell receptacle for detection.

22 Claims, 9 Drawing Sheets s5a

10 s3b

20

20 s4b

METHOD AND KIT FOR IDENTIFYING ANTIMICROBIAL AGENTS AND EFFECTIVE CONCENTRATIONS THEREOF

RELATED APPLICATION

This application claims the benefit of U.S. Provisional Application No. 63/158,061 filed Mar. 8, 2021; the entire contents of Patent Application No. 63/158,061 are hereby incorporated by reference.

GOVERNMENT SUPPORT

This invention was made with government support under DK126572 awarded by the National Institutes of Health. The government has certain rights in the invention.

FIELD OF THE DISCLOSURE

The present disclosure generally relates to microbial organisms and methods to control proliferation thereof, and in particular to methods and systems for identifying antimicrobial agents and effective concentrations of antimicrobial agents.

BACKGROUND

The following paragraphs are provided by way of background to the present disclosure. They are not however an admission that anything discussed therein is prior art or part of the knowledge of persons skilled in the art.

There are many circumstances in which it is desirable to control the proliferation of microbial organisms. Thus, for example, humans and animals can contract infectious microbial pathogens, and develop diseases. Control of microbial infection can prevent potentially fatal diseases in humans and animals, and can ensure that complex medical procedures, such as surgery and chemotherapy, can be safely delivered.

Another example where undesirable microbial growth represents a significant and persistent problem is in the food production and consumption chain. The incidence of food borne microbial pathogens, such as *Salmonella, Listeria*, and *Escherichia coli* present significant costs to the food industry in terms of financial losses and reputational damage, and, and, worse, can threaten human health.

Consequently, a variety of systems and techniques for diagnostic testing and intervention by the administration or application of antimicrobial agents have been developed.

One substantial ongoing challenge associated with the control of the proliferation of microbial organisms is the lag time between initial detection and diagnosis, and the subsequent identification of an efficacious antimicrobial agent. In this respect, the identification of an antimicrobial agent initially requires a diagnosis of a microbial causative agent, and then the identification of an efficacious antimicrobial agent, and further an appropriate dosing or application regimen. In instances where human or animal health are concerned, it is desirable to reduce the time period between an initial diagnosis of a potential microbial infectious disease and the therapeutic intervention by the administration of an antimicrobial agent to a human and animal, in order to thereby reduce the pathological impact of the infectious agent and/or to curtail opportunities for the infection to spread.

Furthermore, antimicrobial resistance (AMR), i.e., the resistance of microbial organisms against antimicrobial agents, represents a significant threat to human and animal health (see: e.g., World Health Organization. (2015). Global action plan on antimicrobial resistance. World Health Organization). In general, AMR has been associated with the injudicious use of antimicrobial agents. In order to address AMR and limit the spread of antimicrobial resistant microorganisms, and the potential transmission of antibiotic resistance determinants to other pathogenic or non-pathogenic microorganisms, the rapid identification of antimicrobial resistant microbial organisms, for example, in a hospital setting is important. Furthermore, rapid identification can enable optimal treatment outcomes and reduce the probability of developing further resistance by informing the selection of the appropriate antimicrobial agent for the appropriate patient.

The ongoing shortcomings of known systems for identifying effective antimicrobial agents necessitate improved systems and techniques. Notably there is a need in the art for systems and techniques for rapid, cost-effective, accurate, rapid and easy-to-use systems for identifying effective antimicrobial agents and efficacious concentrations thereof.

SUMMARY

The following paragraphs are intended to introduce the reader to the more detailed description that follows and not to define or limit the claimed subject matter of the present disclosure.

In one broad aspect, the present disclosure relates to methods and systems for identifying antimicrobial agents.

In another broad aspect, the present disclosure relates to methods and systems for identifying effective concentrations of antimicrobial agents.

Accordingly, in one aspect, in accordance with the teachings herein, the present disclosure provides, in at least one aspect, in at least one embodiment, a method for determining an effective concentration of an antimicrobial agent for inhibiting bacterial growth, the method comprising:

a) transferring a sample containing or suspected to contain living microbial cells to a first plurality of wells of a first multiwell receptacle, the first plurality of wells containing a range of known concentrations of at least one antimicrobial agent, each well of the first plurality of wells further containing bacterial growth medium and bacteriophage capable of infecting the microbial cells, to thereby form assay mixtures in each well of the first plurality of wells;

b) incubating the first multiwell receptacle under conditions sufficient to promote bacterial growth and infection of the bacterial cells by the bacteriophage, and cause the production of progeny bacteriophage in the assay mixtures;

c) transferring the assay mixtures from the first plurality of wells of the first multiwell receptacle to a corresponding second plurality of wells of a second multiwell receptacle, each of the corresponding wells of the second plurality of wells containing primary anti-bacteriophage antibodies to thereby bind the progeny bacteriophage to the primary antibodies and form a primary antibody-bacteriophage complex; and d) detecting the primary antibody-bacteriophage complex in the corresponding second plurality of wells of the second multiwell receptacle, wherein an effective concentration of the antimicrobial agent is a known concentration in one or more wells in the first plurality of wells that corresponds with one or more wells in the second plurality of wells in which the primary antibody-bacteriophage complex is not detected.

In at least one embodiment, in an aspect, the primary antibody can be labeled with a detectable label, and the detecting comprises: detecting the labeled primary antibody-bacteriophage-complex in the second plurality of wells, wherein an effective concentration of the antimicrobial agent is a known concentration in one or more wells in the first plurality of wells that corresponds with one or more wells in the second plurality of wells in which substantially no labeled primary antibody-bacteriophage complex is detected.

In at least one embodiment, in an aspect, the detecting can comprise:

contacting the primary antibody-bacteriophage complex with a secondary anti-bacteriophage antibody labeled with a detectable label to thereby bind the primary antibody-bacteriophage complex to the secondary bacteriophage antibody and form a labeled primary antibody-bacteriophage-secondary antibody complex; and detecting the labeled primary antibody-bacteriophage-secondary antibody complex in the second plurality of wells, wherein an effective concentration of the antimicrobial agent is a known concentration in one or more wells in the first plurality of wells that corresponds with one or more wells in the second plurality of wells in which substantially no labeled primary antibody-bacteriophage-secondary antibody complex is detected.

In at least one embodiment, in an aspect, the first multiwell receptacle can contain a control assay mixture including the bacterial growth medium and the bacteriophage, the control assay mixture not containing antimicrobial agent.

In at least one embodiment, in an aspect, the control assay mixture can include a control sample known to contain the living microbial cells.

In at least one embodiment, in an aspect, the range of known concentrations of antimicrobial agent can be distributed along a row or column of wells in the first multiwell receptacle.

In at least one embodiment, in an aspect, the range of known concentrations can include at least three different known concentrations distributed along the row or column from highest to lowest concentration.

In at least one embodiment, in an aspect, the range of known concentrations of antimicrobial agent can be a serial dilution containing at least three different concentrations.

In at least one embodiment, in an aspect, the serial dilution can be distributed along a row or column of wells in the first multiwell receptacle from highest to lowest concentration.

In at least one embodiment, in an aspect, the multiwell receptacle can contain a plurality of ranges of known concentrations of a corresponding plurality of antimicrobial agents.

In at least one embodiment, in an aspect, each of the ranges of the plurality of ranges can be distributed along a different column or row of wells of the first multiwell receptacle.

In at least one embodiment, in an aspect, each of the ranges of the plurality of ranges can be distributed along a different column or row of wells of the first multiwell receptacle, each range including at least three different known concentrations, each concentration in the range distributed along the wells of a column or row from highest to lowest concentration.

In at least one embodiment, in an aspect, the sample containing or suspected to contain living microbial cells can be a sample containing or suspected to contain microbial cells of two or more microbial species, and the first multiwell receptacle can contain bacteriophage capable of producing progeny in the two or more microbial species.

In at least one embodiment, in an aspect, the sample containing or suspected to contain living microbial cells can be a sample containing or suspected to contain microbial cells of two or more microbial species, and the first multiwell receptacle can contain two or more bacteriophage strains, each bacteriophage strain capable of producing progeny in a single species of the two or more microbial species.

In at least one embodiment, in an aspect, the two or more bacteriophage strains capable of producing progeny in the two or more microbial species can each be contained in separate wells.

In at least one embodiment, in an aspect, each bacteriophage strain of the two or more bacteriophage strains can be distributed along a different row or column of the first multiwell receptacle, each row or column further containing a range of concentrations of the same antimicrobial agent, each range including at least three different known concentrations of the antimicrobial agent, distributed along each row or column from highest to lowest concentration.

In at least one embodiment, in an aspect, the two or more bacteriophage strains capable of producing progeny in the two or more microbial species can both be contained in the same wells to form a mixture of bacteriophage strains in the wells.

In at least one embodiment, in an aspect, the mixture of bacteriophage strains can be distributed along rows or columns of the first multiwell receptacle, each row or column further containing a range of concentrations of a plurality of antimicrobial agents, each range including at least three different known concentrations of each antimicrobial agent, distributed along each row or column from highest to lowest concentration, the second multiwell receptacle containing in a plurality of wells a mixture of two or more primary anti-bacteriophage antibodies in each well of the plurality of wells, the primary anti-bacteriophage antibodies capable of binding each of the bacteriophage strains.

In at least one embodiment, in an aspect, the microbial cells can be human or animal pathogenic microbial cells.

In at least one embodiment, in an aspect, the microbial cells can belong to group genera consisting of *Enterococcus, Staphylococcus, Klebsiella, Acinetobacter, Pseudomonas* and *Enterobacter.*

In at least one embodiment, in an aspect, the microbial cells can belong to the group of species consisting of *Enterococcus faecium, Staphylococcus aureus, Klebsiella pneumoniae, Acinetobacter baumannii, Pseudomonas aeruginosa* and *Enterobacter cloacae.*

In another aspect, in accordance with the teachings herein, the present disclosure provides, in at least one aspect, in at least one embodiment, a kit for determining an effective concentration of an antimicrobial agent for inhibiting bacterial growth, the kit comprising:

a) first multiwell receptacle comprising a first plurality of wells comprising bacteriophage capable of infecting microbial cells; and b) a second multiwell receptacle comprising a corresponding second plurality of wells comprising primary anti-bacteriophage antibodies capable of binding the bacteriophage, together with instructions to determine an effective concentration of an antimicrobial agent for inhibiting bacterial growth by (i) transferring a sample containing or suspected to contain living microbial cells to a first plurality of wells of the first multiwell receptacle, the first plurality of wells containing a range of known concentrations of at least one antimicrobial agent, each well of the first plurality of wells further containing bacterial growth medium, the bacteriophage in the plurality of wells being capable of infecting the microbial cells, to thereby form assay mixtures in each of the wells of the first plurality of wells;

(ii) incubating the first multiwell receptacle under conditions sufficient to promote bacterial growth and infection of the bacterial cells by the bacteriophage, and cause the production of progeny bacteriophage in the assay mixtures;

(iii) transferring the assay mixtures from the first plurality of wells of the first multiwell receptacle to a corresponding second plurality of wells of the second microtiter to thereby bind the progeny bacteriophage to the primary anti-bacteriophage antibodies and form a primary antibody-bacteriophage complex; and (iv) detecting the primary antibody-bacteriophage complex.

In at least one embodiment, in an aspect, the primary antibody can be labeled with a detectable label, and the detecting comprises:

detecting the labeled primary antibody-bacteriophage-complex in the second plurality of wells, wherein an effective concentration of the antimicrobial agent is a known concentration in one or more wells in the first plurality of wells that corresponds with one or more wells in the second plurality of wells in which substantially no labeled primary antibody-bacteriophage complex is detected.

In at least one embodiment, in an aspect, the kit can further comprise a secondary anti-bacteriophage antibody labeled with a detectable label and the detecting can comprise:

contacting the primary antibody-bacteriophage complex with a secondary anti-bacteriophage antibody labeled with a detectable label to thereby bind the primary antibody-bacteriophage complex to the secondary bacteriophage antibody and form a labeled primary antibody-bacteriophage-secondary antibody complex; and detecting the labeled primary antibody-bacteriophage-secondary antibody complex in the second plurality of wells, wherein an effective concentration of the antimicrobial agent is a known concentration in one or more wells in the first plurality of wells that corresponds with one or more wells in the second plurality of wells in which substantially no labeled primary antibody-bacteriophage-secondary antibody complex is detected.

In at least one embodiment, in an aspect, the kit can further comprise bacterial growth medium distributed in the first plurality of wells of the first multiwell receptacle, or in a separate vessel for distribution into the plurality of wells of the first multiwell receptacle.

In at least one embodiment, in an aspect, the first plurality of wells of the first multiwell receptacle can contain a range of known concentrations of at least one antimicrobial agent.

In at least one embodiment, in an aspect, the range of known concentrations of antimicrobial agent can be distributed along a row or column of wells in the first multiwell receptacle.

In at least one embodiment, in an aspect, the range of known concentrations can include at least three different known concentrations distributed along the row or column from highest to lowest concentration.

In at least one embodiment, in an aspect, the range of known concentrations of antimicrobial agent can be a serial dilution containing at least three different concentrations.

In at least one embodiment, in an aspect, the serial dilution can be distributed along a row or column of wells in the first multiwell receptacle from highest to lowest concentration.

In at least one embodiment, in an aspect, the first multiwell receptacle can contain a plurality of ranges of known concentrations of a corresponding plurality of antimicrobial agents.

In at least one embodiment, in an aspect, each of the ranges of the plurality of ranges can be distributed along a different row or column of wells of the first multiwell receptacle.

In at least one embodiment, in an aspect, each of the ranges of the plurality of ranges can be distributed along a different column or row of wells of the first multiwell receptacle, each range including at least three different known concentrations, each concentration in the range distributed along the wells of a column or row from highest to lowest concentration.

In at least one embodiment, in an aspect, the sample containing or suspected to contain living microbial cells can be a sample containing or suspected to contain microbial cells of two or more microbial species, and the multiwell receptacle can contain bacteriophage capable of producing progeny in the two or more microbial species.

In at least one embodiment, in an aspect, the sample containing or suspected to contain living microbial cells can be a sample containing or suspected to contain microbial cells of two or more microbial species, and the first multiwell receptacle can contain two or more bacteriophage strains, each bacteriophage strain capable of producing progeny in a single species of the two or more microbial species.

In at least one embodiment, in an aspect, the two or more bacteriophage strains capable of producing progeny in the two or more microbial species can each be contained in separate wells.

In at least one embodiment, in an aspect, each bacteriophage strain of the two or more bacteriophage strains can be distributed along a different row or column of the first multiwell receptacle, each row or column further containing a range of concentrations of the same antimicrobial agent, each range including at least three different known concentrations of the antimicrobial agent, distributed along each row or column from highest to lowest concentration.

In at least one embodiment, in an aspect, the two or more bacteriophage strains capable of producing progeny in the two or more microbial species can both be contained in the same wells to form a mixture of bacteriophage strains in the wells.

In at least one embodiment, in an aspect, the mixture of bacteriophage strains can be distributed along rows or columns of the first multiwell receptacle, each row or column further containing a range of concentrations of a plurality of antimicrobial agents, each range including at least three different known concentrations of each antimicrobial agent, distributed along each row or column from highest to lowest concentration, the second multiwell receptacle containing in a plurality of wells a mixture of two or more primary anti-bacteriophage antibodies in each well of the plurality of wells, the primary anti-bacteriophage antibodies capable of binding each of the bacteriophage strains.

In at least one embodiment, in an aspect, the microbial cells can be human or animal pathogenic microbial cells.

In at least one embodiment, in an aspect, the microbial cells can belong to the group of genera consisting of *Enterococcus, Staphylococcus, Klebsiella, Acinetobacter, Pseudomonas* and *Enterobacter.*

In at least one embodiment, in an aspect, the microbial cells can belong to the group of species consisting of *Enterococcus faecium, Staphylococcus aureus, Klebsiella pneumoniae, Acinetobacter baumannii, Pseudomonas aeruginosa* and *Enterobacter cloacae.*

In another aspect, in accordance with the teachings herein, the present disclosure provides, in at least one aspect, in at least one embodiment, an assembly of reagents for use in conjunction with a kit or a method of the present disclosure.

In another aspect, in accordance with the teachings herein, the present disclosure provides, in at least one aspect, in at least one embodiment, a use of a kit as described herein for determining an effective concentration of an antimicrobial agent.

Other features and advantages of the present disclosure will become apparent from the following detailed description. It should be understood, however, that the detailed description, while indicating preferred implementations of the present disclosure, is given by way of illustration only, since various changes and modification within the spirit and scope of the disclosure will become apparent to those of skill in the art from the detailed description.

BRIEF DESCRIPTION OF THE DRAWINGS

The disclosure is in the hereinafter provided paragraphs described, by way of example, in relation to the attached figures. The figures provided herein are provided for a better understanding of the example embodiments and to show more clearly how the various embodiments may be carried into effect. The figures are not intended to limit the present disclosure.

Figure 6:
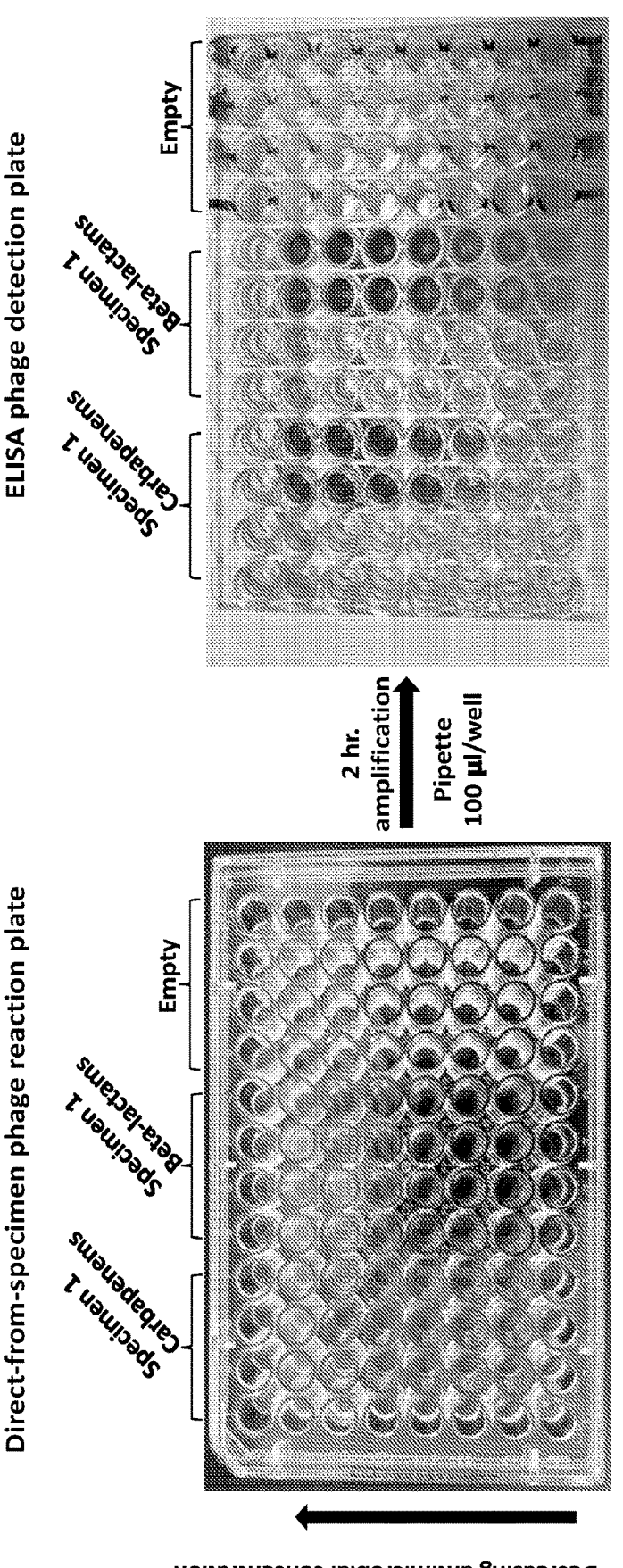

FIG. 6 shows certain experimental results obtained in the performance of an example embodiment of a method of the present disclosure. Shown on the left hand side is a first microtiter plate serving as a reaction plate containing urine samples containing an *E. coli* microbial strain in all wells (excepting the wells labeled as "Empty"), and various dilutions (along rows of wells) of various anti-microbial agents (along columns of wells). Shown on the right hand is a second microtiter plate serving as a detection plate. Phage are colorimetrically (blue) detected in the detection plate.

The figures together with the following detailed description make apparent to those skilled in the art how the disclosure may be implemented in practice.

DETAILED DESCRIPTION

Various processes, methods and systems will be described below to provide at least one example of at least one embodiment of the claimed subject matter. No embodiment described below limits any claimed subject matter and any claimed subject matter may cover processes, methods or systems that differ from those described below. The claimed subject matter is not limited to any process, method or system having all of the features of processes, methods or systems described below, or to features common to multiple processes, methods or systems described below. It is possible that a process, method or system described below is not an embodiment of any claimed subject matter. Any subject matter disclosed in processes, methods or systems described below that is not claimed in this document may be the subject matter of another protective instrument, for example, a continuing patent application, and the applicants, inventors or owners do not intend to abandon, disclaim or dedicate to the public any such subject matter by its disclosure in this document.

As used herein and in the claims, the singular forms, such as "a", "an" and "the" include the plural reference and vice versa unless the context clearly indicates otherwise. Throughout this specification, unless otherwise indicated, the terms "comprise," "comprises" and "comprising" are used inclusively rather than exclusively, so that a stated integer or group of integers may include one or more other non-stated integers or groups of integers. The term "or" is inclusive unless modified, for example, by "either". The term "and/or" is intended to represent an inclusive or. That is "X and/or Y" is intended to mean X or Y or both, for example. As a further example, X, Y and/or Z is intended to mean X or Y or Z or any combination thereof.

When ranges are used herein for physical properties, such as molecular weight, or chemical properties, such as chemical formulae, all combinations and sub-combinations of ranges and specific embodiments therein are intended to be included. Other than in the operating examples, or where otherwise indicated, all numbers expressing quantities of ingredients or reaction conditions used herein should be understood as being modified in all instances by the term "about." The term "about" when referring to a number or a numerical range means that the number or numerical range referred to is an approximation within experimental variability (or within statistical experimental error), and thus the number or numerical range may vary between 1% and 15% of the stated number or numerical range, as will be readily recognized by the context. Furthermore, any range of values described herein is intended to specifically include the limiting values of the range, and any intermediate value or sub-range within the given range, and all such intermediate values and sub-ranges are individually and specifically disclosed (e.g., a range of 1 to 5 includes any number from 1 to 5 such as, but not limited to 1, 1.5, 2, 2.75, 3, 3.90, 4, and 5, for example). Similarly, other terms of degree such as "substantially" and "approximately" as used herein mean a reasonable amount of deviation of the modified term such that the end result is not significantly changed. These terms of degree should be construed as including a deviation of the modified term, such as up to 15% for example, if this deviation would not negate the meaning of the term it modifies.

Unless otherwise defined, scientific and technical terms used in connection with the formulations described herein shall have the meanings that are commonly understood by those of ordinary skill in the art. The terminology used herein is for the purpose of describing particular embodiments only, and is not intended to limit the scope of the present teachings herein, which is defined solely by the claims.

All publications, patents, and patent applications referred to are herein incorporated by reference in their entirety to the same extent as if each individual publication, patent or patent application was specifically indicated to be incorporated by reference in its entirety.

In general, the methods and kits of the present disclosure can be used to identify antimicrobial agents and concentrations thereof which are effective in inhibiting microbial growth. In broad terms, the methods of the present disclosure involve transferring a sample of living microbial cells to a first plurality of wells of a multiwell receptacle, such as a microtiter plate, for example. The plurality of wells contain a range of known concentrations of at least one antimicrobial agent. Furthermore, the wells contain bacteriophage capable of infecting the microbial cells and microbial growth medium. The plates are incubated to produce bacteriophage in the wells. The assay mixtures in the wells are then transferred to a second plurality of corresponding wells of a second multiwell receptacle, such as a microtiter plate, for example. Bacteriophage is then detected in the second microtiter plate, for example, by using a labeled antibody. An effective concentration of the antimicrobial agent is a concentration at which no labeled antibody is detected.

In systems known to the art there exists a considerable lag time between diagnosis of a causative microbial agent and the identification of a suitable antimicrobial agent and an effective concentration thereof. During the lag time the microbial agent may cause damage and/or spread. The method and kit of the of the present disclosure allows a user to assay a sample containing or suspected to contain one or more species of microbial organisms, and rapidly, in a single diagnostic test, identify an antimicrobial agent that inhibits proliferation of the one or more microbial species present in the sample, and a suitable concentration of the antimicrobial agent to inhibit proliferation of the one or more microbial species.

Furthermore, many systems known to the prior art involve isolation of a microbial species from a fluid sample in order to identify an antimicrobial agent and/or suitable concentrations thereof, which may be challenging and/or time consuming, especially when several microbial species are present in the sample. By contrast, the present methods and kits do not require isolation of the microbial species, and the methods of the present disclosure can be practiced directly using the fluid sample. Furthermore, the methods and kits of the present disclosure can be used to assay a sample comprising a mixture of bacterial species.

Furthermore, in the same diagnostic test, one or more microbial species present in the sample may be identified.

Furthermore, the kit of the present disclosure is easy to manufacture and use, and can be implemented in a cost-effective manner.

In what follows selected example embodiments are described with reference to the drawings.

Figure 1:
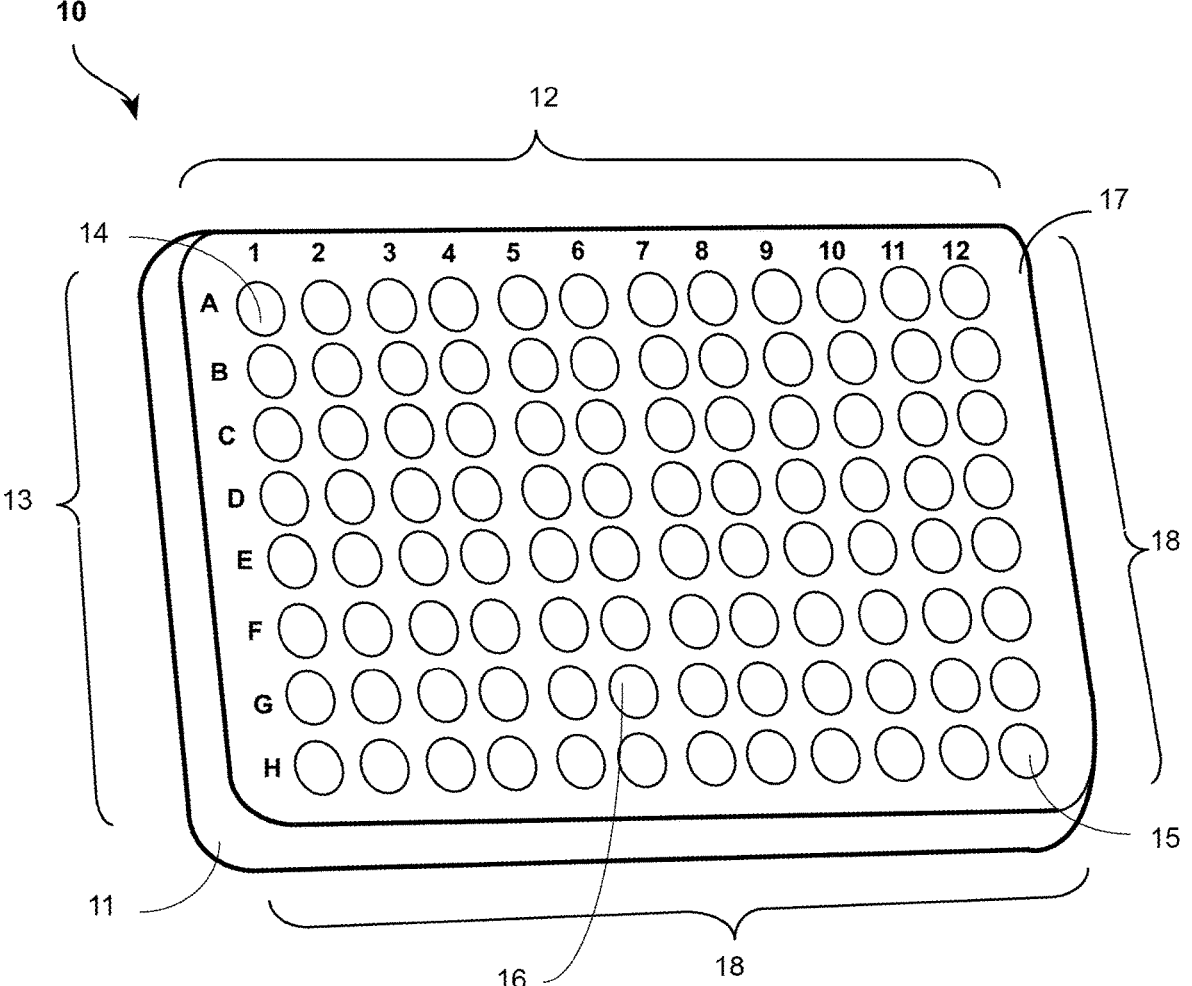
FIG. 1 is a view of an example microtiter plate that can be used to determine an effective concentration of an anti-microbial agent for inhibiting bacterial growth.

Referring initially to FIG. 1, shown therein is an example microtiter plate 10, comprising a housing 11 having a substantially flat top surface 17 and embedded therein and projecting downwards from top surface 17 a rectangular array 18 of generally identical cylindrical wells, forming rows 13 and columns 12. The shape and size of the wells in different embodiments may vary (e.g., V-shaped bottom, U-shaped bottom, flat bottom), however the wells are generally shaped and sized to allow the receipt of a fluid sample from a fluid dispensing device such as a pipette, or a multichannel pipette (not shown). In different embodiments, the fluid volume that can be contained in each well may vary. However, in typical embodiments the microtiter plate is fabricated to include wells which can contain in each well a fluid volume of no more than 5 ml, and no less than 0.01 ml, for example, 0.01 ml, 0.05 ml, 0.1 ml, 0.5 ml, 1 ml, 2.5 ml, or 5 ml. In order to reference individual wells in microtiter plate 10, rows 13 in array 18 are labeled A-H, and columns 12 in array 18 are labeled 1-12. Thus, by way of a few examples only, in array 18 of microtiter plate 10, the location of well 14 may be referenced as A1, the location of well 16 may be referenced as G6, and the location well 15 may be referenced as H12. As will be clear, any individual well in array 18 of microtiter plate 10 may similarly be referenced and identified by a letter-number combination. Furthermore, as can be seen in FIG. 1, or mathematically determined, microtiter plate 10 comprises a rectangular array 18 of 96 wells. The hereinafter described example embodiments, involve the use of a 96 well microtiter plate, having 12 columns and 8 rows, such as shown in FIG. 1. However, other microtiter plates having a different number of wells e.g., 6, 12, 24, 48, 384 or 1536 wells, for example and/or a different number of rows or columns may also be used. Microtiter plates can generally be manufactured using any suitable material, and are preferably manufactured using a plastic, e.g., polypropylene, polystyrene or polycarbonate, by any suitable manufacturing process or technique, including injection molding, for example, and may, for example, be purchased from a manufacturer of plasticware for use in biochemical or chemical assays, such as Thermo Fisher Scientific®, Waltham, Ma (USA), for example. Microtiter plates are particularly convenient multiwell receptacles that can be used in accordance with the present disclosure. It is noted, however, that the methods of the present disclosure may be practiced using other multiwell receptacles (for example, multiwell receptacles which are geometrically shaped differently than a microwell plate) in a manner similar to microtiter plates. In this respect, it is to be understood that microwell plates represent an example of a multiwell receptacle.

Next, example embodiments, 100, 200, 300 and 400 will be described to illustrate the methods and systems of the disclosure. As hereinbefore noted, in an aspect, the methods and kits of the present disclosure allow for the identification of an antimicrobial agent and a concentration thereof which can inhibit microbial growth of a microorganism that is present in a sample fluid.

Use of the microtiter plates in diagnostic assays in accordance with the present disclosure involves the transfer of fluids to the wells of the microtiter plates and the performance of certain operational steps to develop a detectable signal in one or more of the wells which is indicative of the presence of microbial organisms in one or more wells. Broadly speaking, a first and second microtiter plate are prepared by dispensing certain ingredients in the wells of the first and second microtiter plate. A fluid sample known or suspected to include microorganisms is then dispensed in some or all of the wells of the first microtiter plate to generate assay mixtures in each of the wells containing the fluid sample. The assay mixtures are then transferred to the second microtiter plate in which a detectable signal is developed. As is known to those of skill in the art, the dispensing of fluids in microtiter plates may conveniently be accomplished using a fluid dispensing device which can deliver a measured volume of fluid, notably a pipette, including a micropipette or a multichannel micropipette, the latter allowing for a fluid to be simultaneously received by a plurality of wells, including an entire row or column of wells of a microtiter plate. The preparation of the first and second microtiter plate, and the performance of a diagnostic assay, starting with the dispensing of the fluid sample containing microorganisms into the first microtiter plate, can generally conveniently be performed using a micropipette or a multichannel micropipette.

Figure 2A:
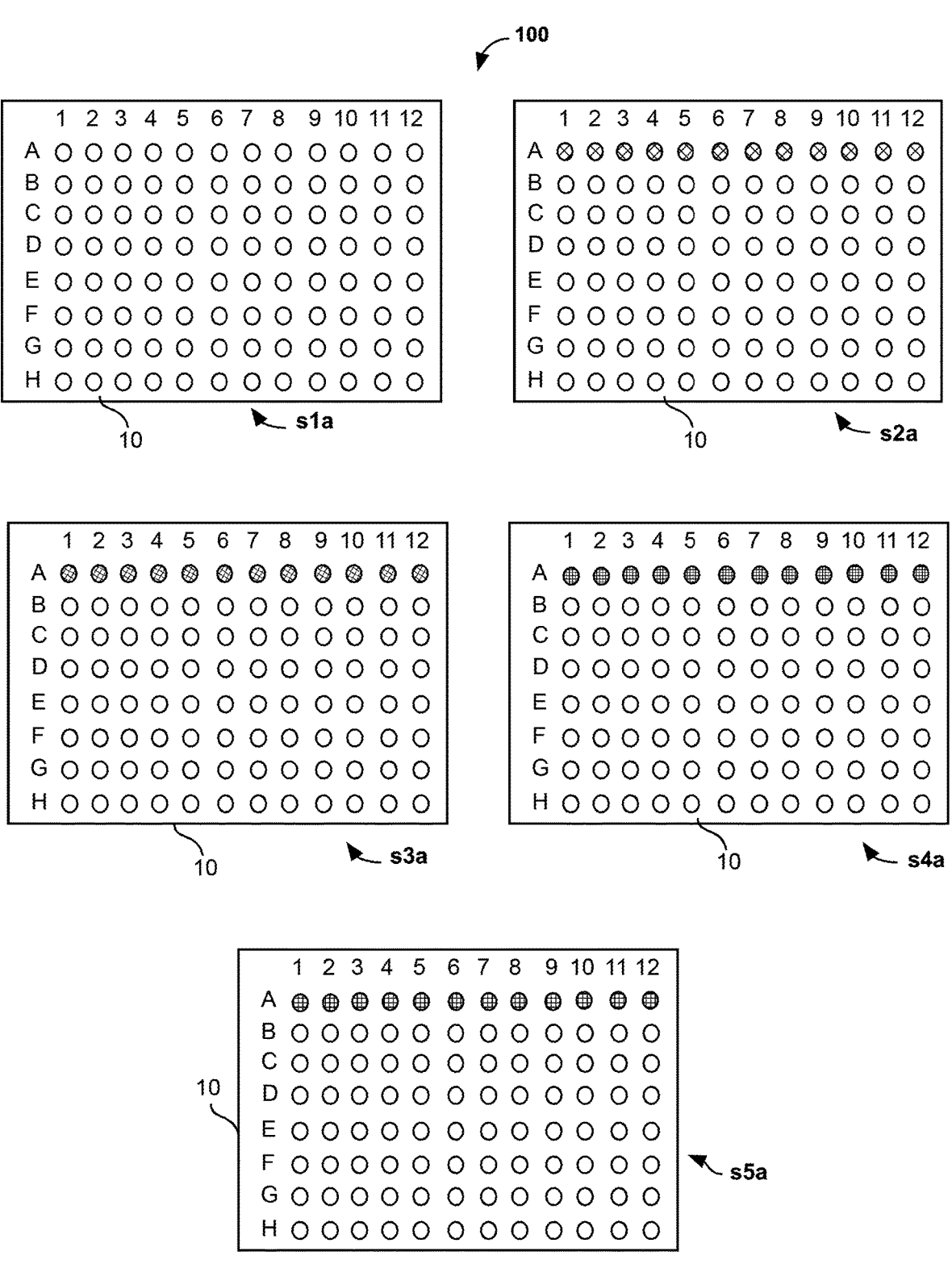
FIG. 2A shows five different example states, s1*a*, s2*a*, s3*a*, s4*a* and s5*a* of a first microtiter plate in accordance with a first example embodiment 100 of the present disclosure.
Figure 2B:
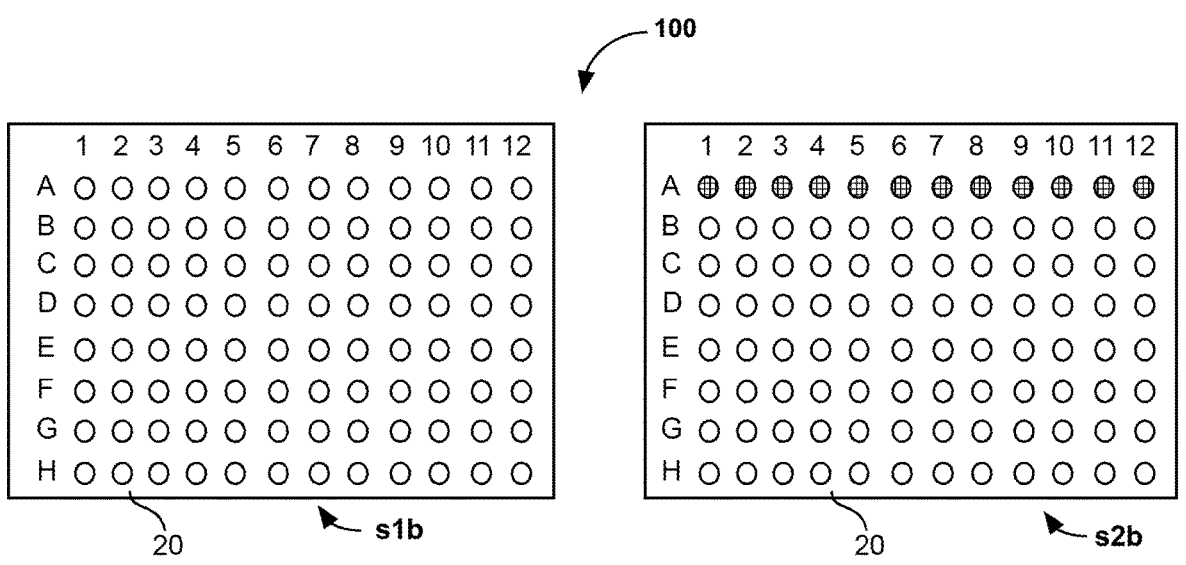
FIG. 2B shows four different example states, s1*b*, s2*b*, s3*b*, and s4*b* of a second microtiter plate in accordance with first example embodiment 100 of the present disclosure.
Figure 2B:
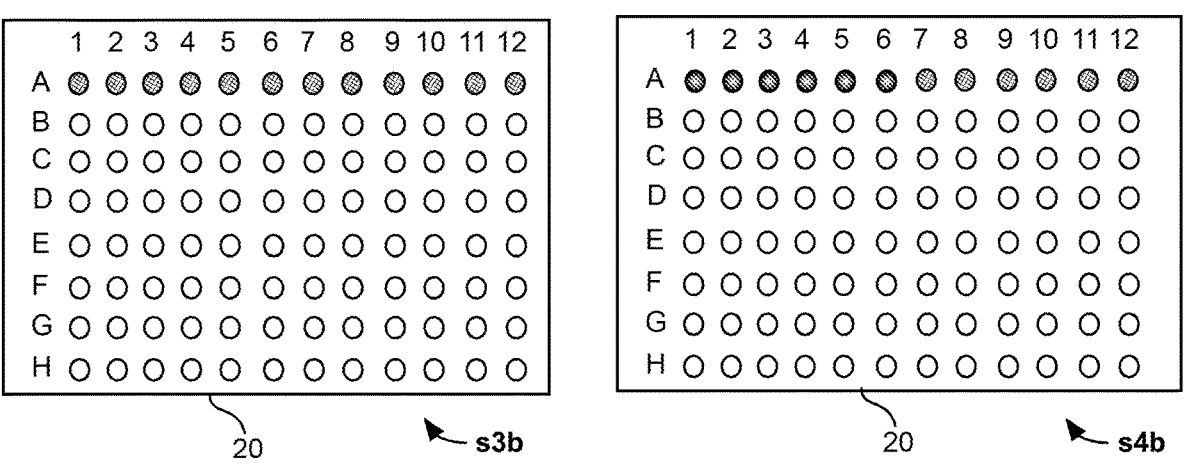

Referring next to FIGS. 2A-2B, shown therein are five different states s1a, s2a, s3a, s4a and s5a of a first microtiter plate 10 (FIG. 2A), and four different states s1b, s2b, s3b and s4b of a second microtiter plate 20 (FIG. 2B) for the purposes of illustrating an example embodiment 100 of a method and kit for the identification of an antimicrobial agent and a concentration thereof which can inhibit microbial growth of a microorganism that is present in a sample fluid.

Referring now to FIG. 2A, at first state s1a, all wells of first microtiter plate 10 are empty, and as such, state s1a reflects a first microtiter plate having been provided.

Continuing to referring to FIG. 2A, at second state s2a, a quantity of an antimicrobial agent has been dispensed in wells A1-A12 of microtiter plate 10 using a fluid dispensing device. In particular, a range of known concentrations of an antimicrobial agent has been dispensed, so that each well A1-A12 contains a different known concentration of the antimicrobial agent. The concentrations of the antimicrobial agent can, for example, be selected so that they are dispensed from the lowest concentration in well A1 to the highest concentration in well A12, or vice versa. The concentrations of antimicrobial agent are generally preferably selected so that at the low end of the concentration range (e.g., dispensed in well A1-A3), the concentration is sufficiently low so that limited or no microbial growth inhibition would be expected to occur, while at the high end of the concentration range (e.g., dispensed in well A10-A12), the concentration of antimicrobial agent is expected to be sufficiently high so that substantial inhibition of microbial growth would be expected to occur. In some embodiments, one well, e.g., well A1 may not contain any antimicrobial agent. In some embodiments, wells A1-A12 may comprise a serial dilution of an antimicrobial agent. The antimicrobial agent may be any known antimicrobial agent or compound suspected to have antimicrobial potency, in particular in relation to the fluid sample comprising a microbial organism to be tested, as hereinafter described. Known antimicrobial agents that may be used in this include beta-lactam based antimicrobial agents, beta-lactam/beta-lactamase inhibitor combination antimicrobial agents, and non-beta-lactam based antimicrobial agents.

Beta-lactam based antimicrobial agents include, without limitation, antimicrobial agents belonging to the classes of penicillins, parenteral and oral cephems, monobactams, and penems.

Examples of antimicrobial agents belonging to the class of penicillins include penicillinase labile penicillins, including penicillin, aminopenicillins (e.g., amoxicillin, ampicillin), carboxypenicillins (e.g., carbenicillin, ticarcillin), and ureidopenicillins (e.g., azlocillin, piperacillin), and penicillinase-stable penicillins, such as cloxacillin, dicloxacillin, nafcillin and oxacillin.

Examples of antimicrobial agents belonging to the class of parenteral cephems include cephalosporins, such as cephalosporin I (e.g., cephazolin, cephalothin), cephalosporin II (e.g., cephamandole, cefonicid), cephalosporin III (e.g., cefixime, cefoperazone, cefotaxime, cefpodoxime, ceftazidime, ceftriaxone), cephalosporin IV (e.g., cefipime, cefiperome), cephalosporin with anti-MRSA activity (e.g., ceftaroline, ceftobiprole) cephamycin (e.g., cefmetazole, cefotetan, cefoxitin), oxacephem (e.g., moxalactam), and siderophorin cephalosporin (e.g., cefiderocol).

Examples of antimicrobial agents belonging to the class of oral cephems include e.g., cefaclor and cefuroxime.

An examples of an antimicrobial agent belonging to the class of monobactams includes e.g., aztreonam.

Examples of antimicrobial agents belonging to the class of penems, include carbapenems (e.g., biapenem, doripenem, ertapenem imipenem, meropenem, razupenem, tebipenem) and penems (e.g., faropenem and sulupenem).

Beta-lactam/beta-lactamase inhibitor combinations include, without limitation, beta-lactam/beta-lactamase inhibitor combinations, such as amoxicillin/K clavulanate, ampicillin/sulbactam, ceftazidime/avibactam, ceftolozane/tazobactam, meropenem/vaborbactam, piperacillin/tazobactam, and ticarcillin/K clavulanate.

Non-beta-lactam based antimicrobial agents include, without limitation, macrolides, such as azithromycin, clarithromycin and erythromycin; phenicols such as chloramphenicol and thiamphenicol; quinolones, such as cinoxacin and garenoxacin; fluoroquinolones, such as ciprofloxacin, ciprofloxacin-S, gatifloxacin, levofloxacin, moxifloxacin, norfloxacin, and ofloxacin; lincosamides, such as clindamycin, inducible clindamycin and lincomycin; polymyxins, such as colistin A RUO, colistin E, P-RUO and polymyxin B; lipopeptides, such as daptomycin and surotomycin; tetracyclins, such as ervacycline, minocycline and tetracycline; fosfomycins, such as fosfomycin RUO; aminoglycosides, such as amikycin, gentamycin, kanamycin and tobramycin; oxazolidones, such as linezolid; nitrofurans, such as nitrofurantoin; ansamycins, such as rifamycins (e.g., rifabutin, rifapentine, rifampin, rifaximin); streptogramins, such as synercid; glycylcyclins, such as tigecycline; folate pathway inhibitors, such as trimethorprim and trimethoprim/sulfamethoxazole; and glycopeptides, such as vancomycin, dalbavancin and ramoplanin.

All of the foregoing example antimicrobial agents may be used in accordance herewith, and dispensed in microtiter plate 10, as herein described to perform the methods of the present disclosure. It is to be understood that the methods and kits of the present disclosure are not limited to specific antimicrobial agents. Any and all antimicrobial agents, including those set forth herein by way of examples, may be used in accordance herewith.

Referring again to FIG. 2A, it is further noted that in other embodiments, fewer dilutions of the antimicrobial agent may be used, and instead of 12 wells, 11 wells (e.g., well A1-A11), 10 wells (e.g., well A1-A10), 9 (e.g., well A1-A9) wells, or even fewer wells of microtiter plate 10 may be used to dispense a range of known concentrations of an antimicrobial agents.

Continuing to refer to FIG. 2A, at third state s3a, a quantity of a microbial growth medium has been dispensed in each of wells A1-A12 of microtiter plate 10. The growth medium may vary but is selected with respect to the microorganism present in the fluid sample to be tested. Suitable microbial growth media include, for example, MRS liquid media, as described in de Man, J. D.; Rogosa, M.; Sharpe, M. E. (1960): "A Medium for the Cultivation of Lactobacilli", J. Appl Bact. 23 (130-135) or modifications thereof. Further growth media that may be used include Trypticase Soy Broth (TSB), Nutrient Broth, Luria-Bertani broth (LB-broth), and ISP medium #1, or modifications thereof, and other microbial growth media known to the art. In general, any medium that allows for growth of the microorganism may be used.

Continuing to refer to FIG. 2A, at fourth state s4a, a quantity of bacteriophage has been dispensed in each of wells A1-A12, notably a bacteriophage capable of infecting the microbial cells present in the fluid sample to be tested. Bacteriophages for different microorganisms are generally art recognized and include, for example, the bacteriophages described by Molineux, I. J. (2006). Chapter 20: The T7 group. In: The Bacteriophages (R. Calendar, ed.), pp. 277. Oxford University Press, Oxford, UK; and Mosig, G. and Eiserlingm F. (2006), Chapter 18: T4 and Related Phages: Structure and Development. In: The Bacteriophages (R. Calendar, ed.), pp, 225. Oxford University Press, Oxford, UK. Bacteriophages may be prepared as described in Bacteriophages: Biology and Applications. E. Kutter and A. Sulakvelidze, 2004, CRC Press, New York, or obtained from a collection such as the American Type Culture Collection (ATCC), for example, ATCC catalogue numbers BAA-1025-B2 (*Escherichia coli* T7 bacteriophage); 11303-B6 (*Escherichia coli* T6 bacteriophage); and 11303-B2 (*Escherichia coli* T2 bacteriophage). Furthermore, bacteriophages may be isolated from sample materials isolated from specific source materials, such as human, animal, or environmental source materials, such as water, for example, surface water samples, wastewater samples, sewage water samples, sludge etc. In general, the bacteriophage may be any known bacteriophage, in particular in relation to the microorganism in the fluid sample to be tested, as hereinafter described.

As is known to those of skill in the art, some bacteriophage strains are capable of infecting all strains, substantially all strains, or all strains of interest, of a bacterial species. Other bacteriophage strains are specific to one or more microbial strains, however, they are not able to infect other strains of a microbial species. Therefore, in some embodiments, the quantity of bacteriophage dispensed in each of wells A1-A12 of microtiter plate 10 may comprise a mixture of bacteriophage strains, wherein the mixture comprises a plurality of bacteriophage strains, such plurality comprising at least a first bacteriophage strain capable of infecting at least a first microbial strain of a microbial species, and a second bacteriophage strain capable of infecting at least a second microbial strain of the same microbial species.

It is noted that states s2a, s3a and s4a represent a sequential dispensing of ingredients in wells A1-A12 of a range of known concentrations of an antimicrobial agent, microbial growth medium and bacteriophage respectively. The order of dispensing may be varied and the three ingredients may be added in any order. Furthermore, following dispensing of each of the three ingredients microtiter plate 10 may be stored, highly preferably under conditions which prevent contamination with ambient microorganisms, until a user wishes to use microtiter plate 10 to test a fluid sample comprising a microbial organism.

Continuing to refer to FIG. 2A, at fifth state s5a, a quantity of a fluid sample containing a microbial organism has been dispensed in each of wells A1-A12. The fluid sample can be any fluid sample known or suspected to contain a microorganism. In some embodiments, the fluid sample containing a microbial organism can be, for example, a human or animal bodily fluid or substance, such as, for example, blood, urine, fluidized fecal material, or fluidized biopsy material. In one embodiment, the microorganism can be a human or animal pathogen, including an infectious pathogen. In other embodiments, the fluid sample can be a fluid sample associated with the food production, processing or consumption chain, including, for example, meat processing or fruit and vegetable processing. In other embodiments, the fluid sample can be a water sample, such as an environmental water sample, for example, a surface water sample (e.g., a river, lake, creek, pond, canal sample), a groundwater sample, a wastewater sample, or a sewage water sample. Furthermore, water samples may be obtained from specific selected geographical locations, for example from an area located in the proximity of industrial activities. In other embodiments, the fluid sample can be a fluid sample associated with biowarfare. In yet other embodiments, the fluid sample can be a fluid sample associated with other industrial processes, including, for example, processes relating to fossil fuel extraction.

It is further noted that in some embodiments, a microbial sample can initially be obtained from a non-liquid source material. Thus, for example, a microbial sample can be recovered from a solid surface, using, for example, a microbial collection device, such as a generally sterile wipe, or swab, or a sample containing airborne microorganisms can be collected using a filter, such as a high-efficiency particulate air (HEPA) filter, to trap airborne microorganisms. The microbial collection devices are subsequently processed to obtain a fluidized sample containing the recovered microorganisms, for example, by immersing the collection device in sterile water or a buffer.

Thus, it will be clear that the methods of the present disclosure may be used to evaluate a sample containing microbial organisms obtained from an extremely wide variety of source materials. In principle, any source material containing microbial organisms or suspected to contain microorganisms can be selected and used in accordance with the present disclosure.

The microorganisms may be any living microorganisms, including any living bacterial cells, yeast cells, mould cells and mycobacterial cells, including any family, genus, subgenus, species, subspecies, variety, or strains thereof.

In specific example embodiments, the cells may be living bacterial cells belonging to a bacterial genus selected from *Enterococcus, Staphylococcus, Klebsiella, Acinetobacter, Pseudomonas* and *Enterobacter.*

In further specific example embodiments, the cells may be living bacterial cells belonging to a bacterial species selected from *Enterococcus faecium, Staphylococcus aureus, Klebsiella pneumoniae, Acinetobacter baumannii, Pseudomonas aeruginosa* and *Enterobacter cloacae.*

In further embodiments, the cells may be bacterial cells selected from *Abiotrophia defectiva, Achromobacter dinitrificans, Achromobacter xylosoxidans, Acinetobacter baumannii/nosocomialis, Acinetobacter calcoaceticus, Acineto-* bacter haemolyticus, Acinetobacter johnsonii, Acinetobacter junii, Acinetobacter lwoffii, Acinetobacter nosocomialis, Acinetobacter pittii, Acinetobacter radioresistens, Acinetobacter ursingii, Actinomyces bovis, Actinomyces europaeus, Actinomyces funkei, Actinomyces graevenitzii, Actinomyces hyovaginalis, Actinomyces israelii, Actinomyces meyeri, Actinomyces naeslundii, Actinomyces neuii, Actinomyces odontolyticus, Actinomyces oris, Actinomyces radingae, Actinomyces turicensis, Actinomyces urogenitalis, Actinotignum schaalii, Aerococcus sanguinicola, Aerococcus urinae, Aerococcus viridans, Aeromonas salmonicida, Aeromonas hydrophila/caviae, Aeromonas jandaei, Aeromonas punctata (caviae), Aeromonas sobria, Aggregatibacter actinomycetemcomitans, Aggregatibacter aphrophilus, Aggregatibacter segnis, Alcaligenes faecalis, Alloiococcus otitis, Alloscardovia omnicolens, Anaerococcus murdochii, Anaerococcus vaginalis, Arthrobacter cumminsii, Bacteroides caccae, Bacteroides eggerthii, Bacteroides fragilis, Bacteroides nordii, Bacteroides ovatus, Bacteroides pyogenes, Bacteroides salyersiae, Bacteroides stercoris, Bacteroides thetaiotaomicron, Bacteroides uniformis, Bacteroides vulgatus, Bifidobacterium breve, Bibliophila wadsworthia, Bordetella avium, Bordetella bronchiseptica, Bordetella hinzii, Bordetella parapertussis, Bordetella pertussis, Brevibacterium casei, Brevundimonas diminutam, Brevundimonas vesicularis, Brucella spp. Burkholderia cenocepacia, Burkholderia cepacian, Burkholderia contaminans, Burkholderia gladioli, Burkholderia multivorans, Burkholderia vietnamienis, Campylobacter coli, Campylobacter jejuni, Campylobacter rectus, Campylobacter ureolyticus, Capnocytophaga ochracea, Capnocytophaga sputigena, Cedecea davisae, Cedecea lapagei, Chryseobacterium gleum, Chryseobacterium indologenes, Citrobacter amalonaticus, Citrobacter braakii, Citrobacter farmer, Citrobacter freundii, Citrobacter koseri, Citrobacter youngae, Clostridium baratii, Clostridium beijerinckii, Clostridium bifermentans, Clostridium botulinum, Clostridium butyricum, Clostridium cadaveris, Clostridium clostridioforme, Clostridium difficile, Clostridium innocuum, Clostrium novyi, Clostridium paraputrificum, Clostridium perfringens, Clostridium ramosum, Clostridium septicum, Clostridium sordellii, Clostridium sporogenes/Clostridium tedium, Clostridium tetani, Comamonas testosterone, Corynebacterium accolens, Corynebacterium afermentans, Corynebacterium amycolatum Corynebacterium aurimucosum, Corynebacterium bovis, Corynebacterium coyleae, Corynebacterium diphtheriae, Corynebacterium freneyi, Corynebacterium glucuronolyticum, Corynebacterium glutamicum, Corynebacterium jeikeium, Corynebacterium kroppenstedtii, Corynebacterium macginleyi, Corynebacterium minutissimum, Corynebacterium mucifaciens/ureicelerivorans, Corynebacterium propinquum, Corynebacterium pseudodiphtheriticum, Corynebacterium pseudotuberculosis, Corynebacterium resistens, Corynebacterium riegelii, Corynebacterium striatum, Corynebacterium tuberculostearicum, Corynebacterium ulcerans, Corynebacterium urealyticum, Corynebacterium xerosis, Cronobacter muytjensii, Cronobacter sakazakii, cronobacter turicensis, Cupriavidus pauculus, Curtobacterium flaccumfaciens, Delftia acidovorans, Dermabacter hominis, Dermacoccus nishinomiyaensis, Edwardsiella hoshinae, Edwardsiella tarda, Eikenella corrodens, Elizabethkingia anopheles, Elizabethkingia meningoseptica, Elizabethkingia miricola, Enterobacter aerogenes, Enterobacter amnigenus, Enterobacter asburiae, Enterobacter cancerogenus, Enterobacter cloacae, Enterobacter hormaechei, Enterobacter kobei, Enterobacter ludwigii, Enterococcus avium, Enterococcus casseliflavus, Enterococcus durans, Enterococcus faecalis, Enterococcus faecium, Enterococcus gallinarum, Enterococcus hirae, Enterococcus mundtii, Enterococcus raffinosus, Escherichia coli, Escherichia fergusonii, Escherichia hermannii, Escherichia vulneris, Ewingella americana, Facklamia hominis, Finegoldia magna, Fluoribacter bozemanae, Fusobacterium canifelinum, Fusobacterium necrophorum, Fusobacterium nucleatum, Fusobacterium periodonticum, Gardnerella vaginalis, Gemella haemolysans, Gemella morbillorum, Gemella sanguinis, Granulicatella adiacens, Haemophilus haemolyticus, Haemophilus influenzae, Haemophilus parahaemolyticus, Haemophilus parainfluenzae, Hafnia alvei, Hathewaya histolytica, Helcococcus kunzii, Kingella denitrificans, Kingella kingae, Klebsiella oxytoca/Raoultella ornithinolytica, Klebsiella pneumoniae, Klebsiella variicola, Kluyvera ascorbate, Kluyvera cryocrescens, Kluyvera intermedia, Kocuria kristinae, Kocuria rhizophila, Kodamaea ohmeri, Kytococcus sedentarius, Lactobacillus gasseri, Lactobacillus jensenii, Lactobacillus rhamnosus, Lactococcus garvieae, Lactococcus lactis, Leclercia adecarboxylata, Legionella longbeachae, Legionella pneumophila, Lelliottia amnigena, Leuconostoc citreum, Leuconostoc mesenteroides, Leuconostoc pseudomesenteroides, Listeria monocytogenes, Macrococcus caseolyticus, Malassezia furfur, Malassezia pachydermatis, Mannheimia haemolytica, Micrococcus luteus, Micrococcus lylae, Mobiluncus curtisii, Moraxella sg Branhamella catarrhalis, Moraxella catarrhalis, Moraxella lacunata, Moraxella sg Moraxella nonliquefaciens, Moraxella sg Moraxella osloensis, Morganella morganii, Myroides odoratimimus, Myroides odoratus, Neisseria bacilliformis, Neisseria cinerea, Neisseria elongate, Neisseria flavescens/subflava, Neisseria gonorrhoeae, Neisseria lactamica, Neisseria meningitidis, Neisseria mucosa, Neisseria sicca, Neisseria weaver, Nocardia abscessus, Nocardia Africana, Nocardia asteroids, Nocardia brasiliensis, Nocardia cyriacigeorgica, Nocardia farcinica, Nocardia nova, Nocardia otitidiscaviarum, Nocardia paucivorans, Nocardia pseudobrasiliensis, Nocardia transvalensis, Nocardia veterana, Nocardia wallacei, Ochrobactrum anthropic, Oligella ureolytica, Oligella urethralis, Paeniclostridium sordellii, Pantoea agglomerans, Parabacteroides distasonis, Parabacteroides dispera, Parabacteroides goldsteinii, Parabacteroides johnsonii/merdae, Paraclostridium bifermentans, Parvimonas micra, Pasteurella multocida, Pediococcus acidilactici, Pediococcus pentosaceus, Peptoniphilus asaccharolyticus, Peptoniphilus harei, Peptostreptococcus anaerobius, Plesiomonas shigelloides, Pluralibacter gergoviae, Porphyromonas asaccharolytica/uenonis, Porphyromonas gingivalis, Porphyromonas somerae, Prevotella bivia, Prevotella buccae, Prevotella denticola, Prevotella intermedia, Prevotella loescheii, Prevotella melaninogenica, Prevotella oralis, Prevotella oris, Propionibacterium acidipropionici, Propionibacterium acnes, Propionibacterium avidum Propionibacterium granulosum, Propionibacterium propionicum, Proteus mirabilis, Proteus penneri, Proteus vulgaris, Providencia alcalifaciens Providencia rettgeri Providencia rustigianii Providencia stuartii, Pseudomonas aeruginosa, Pseudomonas alcaligenes, Pseudomonas fluorescens, Pseudomonas luteola, Pseudomonas mendocina, Pseudomonas oryzihabitans, Pseudomonas putida, Pseudomonas stutzeri, Ralstonia pickettii, Raoultella ornithinolytica, Raoultella planticola, Raoultella terrigena, Rhizobium radiobacter, Rhodotorula mucilaginosa, Rothia aeria, Rothia dentocariosa, Rothia mucilaginosa Salmonella enterica, Saprochaete capitata, Serratia ficaria, Serratia fonticola, Serratia grimesii, Serratia liquefaciens, Serratia marcescens, Serratia odorifera,

*Serratia plymuthica, Serratia proteamaculans, Serratia quinivorans, Serratia rubidaea, Shewanella putrefaciens, Sphingobacterium multivorum, Sphingobacterium spiritivorum, Sphingomonas paucimobilis, Staphylococcus aureus, Staphylococcus auricularis Staphylococcus capitis, Staphylococcus caprae, Staphylococcus carnosus, Staphylococcus chromogenes, Staphylococcus cohnii, Staphylococcus delphini, Staphylococcus epidermidis, Staphylococcus equorum, Staphylococcus fells, Staphylococcus haemolyticus, Staphylococcus hominis, Staphylococcus hyicus, Staphylococcus intermedius, Staphylococcus lentus, Staphylococcus lugdunensis, Staphylococcus pasteuri, Staphylococcus pettenkoferi, Staphylococcus pseudintermedius, Staphylococcus saccharolyticus, Staphylococcus saprophyticus, Staphylococcus schleiferi, Staphylococcus sciuri, Staphylococcus simulans, Staphylococcus vitulinus, Staphylococcus warneri, Staphylococcus xylosus, Stenotrophomonas maltophilia, Streptococcus agalactiae, Streptococcus anginosus, Streptococcus canis, Streptococcus constellatus, Streptococcus cristatus, Streptococcus dysgalactiae, Streptococcus equi, Streptococcus equinus, Streptococcus gallolyticus, Streptococcus gordonii, Streptococcus infantarius, Streptococcus intermedius, Streptococcus lutetiensis, Streptococcus mitis/oralis, Streptococcus mutans, Streptococcus parasanguinis, Streptococcus pneumoniae, Streptococcus pyogenes, Streptococcus salivarius/vestibularis, Streptococcus sanguinis, Streptococcus sobrinus, Streptococcus suis, Streptococcus thermophilus, Streptococcus uberis, Sutterella wadsworthensis, Tannerella forsythia, Trueperella bernardiae, Turicella otitidis, Vagococcus fluvialis, Veillonella dispar, Veillonella parvula, Vibrio alginolyticus, Vibrio cholerae, Vibrio fluvialis, Vibrio metschnikovii, Vibrio mimicus, Vibrio parahaemolyticus, Vibrio vulnificus, Weeksella virosa, Yersinia enterocolitica, Yersinia frederiksenii, Yersinia intermedia, Yersinia kristensenii, Yersinia pseudotuberculosis,* and *Yersinia ruckeri,*

In further embodiments, the cells may be yeast cells selected from *Candida albicans, Candida auris, Candida boidinii, Candida dubliniensis, Candida duobushaemulonii, Candida famata, Candida glabrata Candida guilliermondii, Candida haemulonis, Candida inconspicua, Candida intermedia, Candida kefyr, Candida krusei, Candida lambica, Candida lipolytica, Candida Lusitaniae, Candida metapsilosis, Candida norvegensis, Candida orthopsilosis, Candida parapsilosis, Candida pararugosa, Candida pelliculosa, Candida rugosa, Candida tropicalis, Candida utilis, Candida valida, Candida zeylanoides, Cryptococcus gattii, Cryptococcus neoformans, Cryptococcus neoformans, Cyberlindnera jadinii, Geotrichum candidum, Geotrichum capitatum, Kloeckera apiculate, Malassezia furfur, Malassezia pachydermatis, Pichia ohmeri, Pichia pastoris, Rhodotorula mucilaginosa, Saccharomyces cerevisiae, Trichosporon asahii, Trichosporon inkin,* and *Trichosporon mucoides.*

In further embodiments, the cells may be mould cells selected from *Acremonium sclerotigenum, Alternaria alternata, Aspergillus brasiliensis, Aspergillus calidoustus/ustus, Aspergillus flavus/oryzae, Aspergillus fumigatus, Aspergillus lentulus, Aspergillus nidulans, Aspergillus niger, Aspergillus sydowii, Aspergillus terreus, Aspergillus versicolor, Blastomyces dermatitidis, Cladophialophora bantiana, Coccidioides immitis/posadasii, Curvularia hawaiiensis, Curvularia spicifera, Epidermophyton floccosum, Exophiala dermatitidis, Exophiala xenobiotica, Exserohilum rostratum, Fusarium oxysporum, Fusarium proliferatum, Fusarium solani, Histoplasma capsulatum, Lecythophora hoffmannii, Lichtheimia corymbifera, Microsporum audouinii, Microsporum canis, Microsporum gypseum, Mucor*

*racemosus, Paecilomyces variotii, Penicillium chrysogenum, Pseudallescheria boydii, Purpureocillium lilacinum, Rasamsonia argillacea, Rhizopus arrhizus, Rhizopus microspores, Sarocladium kiliense, Scedosporium apiospermum, Scedosporium prolificans, Sporothrix schenckii, Trichophyton interdigitale, Trichophyton rubrum, Trichophyton tonsurans, Trichophyton verrucosum, Trichophyton violaceum, Trichosporon asahii, Trichosporon dermatis/mucoides,* and *Trichosporon inkin.*

In further embodiments, the cells may be mycobacterial cells selected from *Mycobacterium abscessus, Mycobacterium avium, Mycobacterium chelonae, Mycobacterium fortuitum, Mycobacterium gordonae, Mycobacterium haemophilum, Mycobacterium immunogenum, Mycobacterium intracellulare, Mycobacterium kansasii, Mycobacterium lentiflavum, Mycobacterium leprae, Mycobacterium malmoense, Mycobacterium marinum, Mycobacterium mucogenicum, Mycobacterium scrofulaceum, Mycobacterium simiae, Mycobacterium smegmatis, Mycobacterium szulgai, Mycobacterium tuberculosis,* and *Mycobacterium xenopi.*

In general, the fluid sample containing or suspected to contain a microorganism may be any and all fluid samples containing or suspected to contain any microorganism. It is to be specifically understood that the methods and systems of the present disclosure are not limited by the fluid sample or the microbial cell, and any fluid sample containing or suspected to contain any living microorganism may be selected and used in accordance with the present disclosure.

Upon dispensing of the fluid sample in each of wells A1-A12 of microtiter plate 10, an assay mixture can be said to be formed in each well, and microtiter plate 10 is then incubated under conditions that allow for growth of the microbial cells in the growth medium present in wells A1-A12, for example, at temperatures ranging from about 20° C. to about 40° C., or ranging from about 25° C. to about 37° C. Furthermore, the incubation conditions are conditions which permit the infection of the bacterial cells that are being grown by the bacteriophage present in wells A1-A12, and, subsequently, the production of progeny bacteriophage. The incubation time may vary but can, for example, be as short as about 20 minutes and up to about 300 minutes, for example, about 20 minutes, about 60 minutes, about 120 minutes, about 180 minutes, about 240 minutes, or about 300 minutes. As is appreciated by those of skill in the art, conditions for growth of bacterial cells and infection by bacteriophage can vary depending on the microbial species. These conditions are known to the art for many microbial species, or they may be established through routine experimentation, as necessary, for example, by growing a specific microbial species under a range of different conditions (e.g., at different temperatures, using different growth media, at different atmospheric conditions, using different growth times etc.) and identifying suitable conditions that allows growth of the microbial cells and infection by bacteriophage.

Referring next to FIG. 2B, at first state s1*b*, all wells of first microtiter plate 10 are empty, and as such, state s1*b* reflects a second microtiter plate having been provided.

Continuing to refer to FIG. 2B, at second state s2*b*, a quantity of a primary anti-bacteriophage antibody has been dispensed in wells A1-A12 of microtiter plate 20. The primary anti-bacteriophage antibodies are antibodies which are able to specifically bind the progeny bacteriophage dispensed in wells A1-A12 of microtiter plate 10. Examples of primary anti-bacteriophage antibodies that may be used are polyclonal antibodies such as rabbit, murine, lama anti-bacteriophage antibodies, as well as monoclonal anti-bodies. Suitable anti-bacteriophage antibodies may be purchased, for example, from Fisher Scientific® (Waltham, MA, USA) (see: e.g., catalogue number 71-530-3) or Novus Biologicals®, Centennial, CO, USA) (see: e.g., catalogue number NBP3-05788). Further examples of anti-bacteriophage antibodies may be found in Beckman, T. M. et al., 1995, Immunology 1, 53-54. In order to dispense the primary anti-bacteriophage antibodies, the antibodies may initially be included in a solvent, such as phosphate buffered saline at a pH of about 7, or a carbonate/bicarbonate buffer at pH>9, for example, and the microplates may subsequently be dried to adhere and immobilize the primary anti-bacteriophage antibodies and form a coating of anti-bacteriophage antibodies onto the well surface. Furthermore, primary anti-bacteriophage antibodies may be bound to the microtiter plate using an electrostatically charged microtiter plate to facilitate binding of the antibodies. Other suitable methods to bind anti-bacteriophage antibodies onto the well surface may be selected and used by those of skill in the art, as desired. Following dispensing of the primary anti-bacteriophage antibodies, microtiter plate 20 may be stored, until a user wishes to use microtiter plate 20 to test a fluid sample comprising a microbial organism.

Continuing to refer to FIG. 2B, at third state s3*b* a quantity of the assay mixture from wells A1-A12 of microtiter plate 10, as shown in state s5*a* in FIG. 2A, and following incubation of microtiter plate 10, as hereinbefore described, has been transferred to microtiter plate 20. In particular, assay mixture is transferred from the wells in microtiter plate 10 to the corresponding wells in microtiter plate 20, i.e., assay mixture from well A1 of microtiter plate 10 is transferred to well A1 of microtiter plate 20, assay mixture from well A2 of microtiter plate 10 is transferred to well A2 of microtiter plate 20, assay mixture from well A3 of microtiter plate 10 is transferred to well A3 of microtiter plate 20, and so on. Such of the assay mixtures that contain progeny bacteriophage bind to the primary anti-bacteriophage antibodies present in wells A1-A12 of microtiter plate 20, and upon binding form an immobilized primary antibody-bacteriophage complex in wells A1-A12.

Figure 2C:
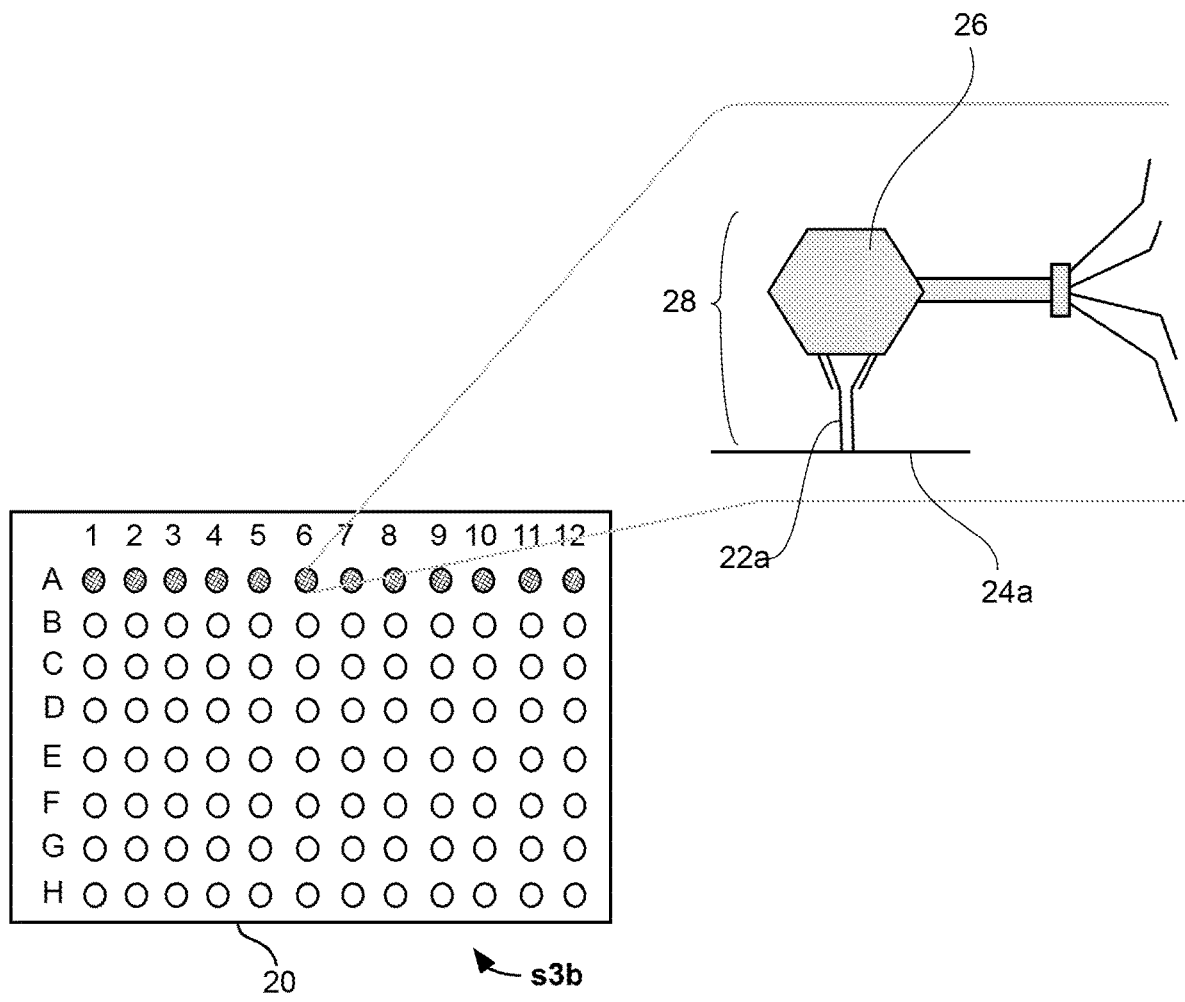
FIG. 2C further illustrates example state s3*b* of first example embodiment 100 of the present disclosure.

Referring now to FIG. 2C, third state s3*b* is further illustrated therein by a schematic view, at a molecular level, of the well inner surface 24*a* of well A6, to which primary anti-bacteriophage antibody 22*a* has been adhered. Together, primary antibody-bacteriophage antibody 22*a* and bacteriophage 26 form immobilized primary antibody-bacteriophage complex 28.

Continuing to refer to FIG. 2B, at fourth state s2*d*, secondary anti-bacteriophage antibody labeled with a detectable label has been dispensed in each of wells A1-A12 of microtiter plate 20. Assay mixtures comprising progeny bacteriophage, in the form of primary antibody-bacteriophage complex bind to the secondary anti-bacteriophage antibody dispensed in wells A1-A12 of microtiter plate 20, and upon binding form a labeled primary antibody-bacteriophage-secondary antibody complex in such of wells A1-A12 which contain bacteriophage in the form of primary antibody-bacteriophage complex. Excess labeled secondary antibody may be washed out using a washing buffer. Labeled antibodies are known to the art and include, for example, fluorophore labeled antibodies, or biotinylated antibodies which may be detected using streptavidin conjugated to, for example, the enzymes horseradish peroxidase (HRP) or alkaline phosphatase (AP). The enzymes are able to enzymatically convert a substrate to produce a colored, fluorescent or chemiluminescent product. Colorimetrically detectable substrates include, for example, 3,3',5,5"-tetramethylbenzidine (TMB), o-phenylenediamine (OPD) and (2,2'-azino-di-(3-ethyl-benzothiazoline-6-sulphonic acid) (ABTS) for horseradish peroxidase and p-nitrophenyl phosphate (PNPP) for alkaline phosphatase. Chemiluminescent substrates for horseradish peroxidase include, for example, 10-acetyl-3,7-dihydroxyphenoxazine (ADHP), and Quantablu™ substrate (Thermo Fisher®, Rockford, III #1856187). A further labeled primary/secondary labeled antibody combination that may be used includes a biotinylated primary antibody and a streptavidin labeled secondary antibody (see: Lakshmipriya T, Gopinath S C, Tang T H. Biotin-Streptavidin Competition Mediates Sensitive Detection of Biomolecules in Enzyme Linked Immunosorbent Assay. *PLoS One.* 2016; 11(3):e0151153. Published 2016 Mar. 8. Doi:10.1371/journal.pone.015115a).

The signal can be measured using a spectrophotometric microtiter plate reader, a fluorometer with appropriate filters, or a luminometer set to measure the total light output. Other techniques for labeling antibodies and detection techniques and equipment suitable to detect labeled antibodies are known to the art and may be used. It is noted that the foregoing detection methodology is also known in the art as enzyme-linked immunosorbent assay (ELISA), and in general ELISA techniques and reaction conditions known to the art may be used to practice the methods of the present disclosure.

It is noted that in some embodiments, prior to transfer of the assay mixture from wells A1-A12 of microtiter plate 10 to microtiter plate 20, microtiter plate 20 can be treated with a blocking buffer containing a non-pertinent protein, for example, bovine serum albumin or casein, to prevent potential non-specific binding of the secondary antibody to the microtiter plate, and thereby improve the signal to noise ratio.

In the shown example embodiment in FIG. 2B, labeled antibody is detected in wells A1, A2, A3, A4, A5, and A6. No labeled antibody is detected in wells A7, A8, A9, A10, A11, and A12. Thus, bacteriophage is present in wells A1, A2, A3, A4, A5, and A6 of microtiter plate 20. Furthermore, bacterial cells therefore were present in corresponding wells A1, A2, A3, A4, A5, and A6 of microtiter plate 10, and, thus, the specific known concentrations of antimicrobial agent present in wells A1, A2, A3, A4, A5, and A6 were insufficient to inhibit bacterial growth. By contrast, in wells A7, A8, A9, A10, A11, and A12, no bacteriophage is present. Furthermore, no bacterial cells therefore were present in corresponding wells A7, A8, A9, A10, A11, and A12 of microtiter plate 10, and, thus, the specific known concentrations of antimicrobial agent present in wells A7, A8, A9, A10, A11, or A12 were each sufficient to inhibit bacterial growth.

Figure 2D:
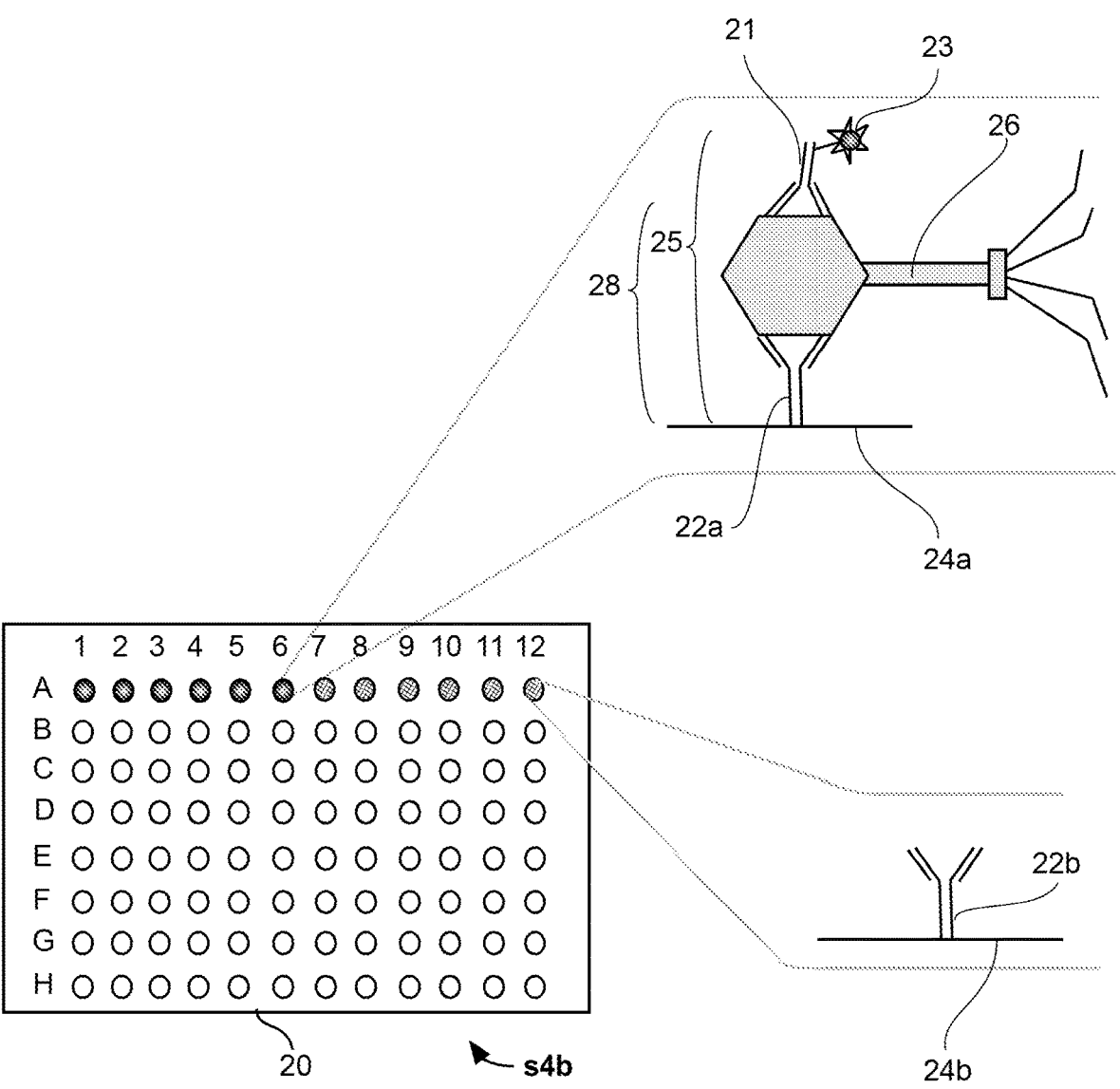
FIG. 2D further illustrates example state s4*b* of first example embodiment 100 of the present disclosure.

Referring now to FIG. 2D, fourth state s2*d* is further illustrated therein by a schematic view, at a molecular level, of the well inner surface 24*a* of well A6, to which primary anti-bacteriophage antibody 22*s* has been adhered. Together, primary anti-bacteriophage antibody 22*a* and bacteriophage 26 form primary antibody-bacteriophage complex 28. Labeled secondary anti-bacteriophage antibody 21 comprises label 23, and is bound to bacteriophage 26. Together, primary antibody-bacteriophage antibody 22*a*, bacteriophage 26 and labeled secondary anti-bacteriophage antibody 21 form labeled primary antibody-bacteriophage-secondary antibody complex 25.

Referring further to FIG. 2D, inner surface 24*b* of well A12 comprises primary antibody 22*b*. Due to the absence of bacteriophage in well A12 of microtiter plate 20, as a result of a sufficiently high concentration of antimicrobial agent and the absence of microbial growth in the corresponding well A12 of microtiter plate 10, no labeled secondary antibody is present or detected in well A12 of microtiter plate 20.

In another embodiment, instead of using a secondary labeled antibody to detect bacteriophage, the primary antibody may be a labeled antibody. Bacteriophage then can be detected upon the formation of a bacteriophage-labeled primary antibody complex in the wells of second microtiter plate. As will be clear, analogous to the embodiment shown in FIGS. 2A-2D, the absence of detectable bacteriophage indicates the presence of a sufficiently high concentration of antimicrobial agent and the absence of microbial growth in the wells of the first microtiter plate. Conversely, detection of bacteriophage, indicates a concentration of microbial agent in the wells of the first microtiter plate which is insufficient to prevent microbial growth.

As hereinbefore noted, in some embodiments, the quantity of bacteriophage dispensed in each of wells A1-A12 may comprise a mixture of bacteriophage strains, wherein the mixture comprises a plurality of bacteriophage strains, such plurality comprising at least a first bacteriophage strain capable of infecting at least a first microbial strain of a microbial species, and a second bacteriophage strain capable of infecting at least a second microbial strain of the same microbial species. In such embodiment, primary antibody-bacteriophage antibody may bind to the first bacteriophage strain in the event a bacterial strain specific to the first bacteriophage strain is present in the fluid sample. Furthermore, Primary antibody-bacteriophage antibody may bind to the second bacteriophage strain in the event a bacterial strain specific to the second bacteriophage strain is present in the fluid sample. Finally, primary antibody-bacteriophage antibody may bind to the first and second bacteriophage strain in the event a first bacterial strain specific to the first bacteriophage strain is present in the fluid sample and a second bacterial strain specific to the second bacteriophage strain is present in the fluid sample. The subsequent detection of labeled antibody reveals (as shown in state s4b) that at least one microbial strain, which at least one of the bacteriophages can infect, is present in the fluid sample. It is noted that in order to further distinguish between different bacterial strains, quantities of a first bacteriophage strain capable of infecting at least a first microbial strain of a microbial species can be dispensed in, for example, wells A1-A12, and a second bacteriophage strain capable of infecting at least a second microbial strain of a microbial species can be dispensed in, for example, wells B1-B12.

It is noted that in some embodiments, in addition to transferring a fluid sample containing or suspected to contain a microorganism to wells A1 to A12 of microtiter plate 10, a further fluid sample known to contain the microorganism may be transferred to wells of microtiter plate 10, e.g., wells B1 to B12 of microtiter plate 10. At state s4b a signal will then be detected at least in a well (e.g., B1) not containing any antimicrobial agent.

Figure 3:
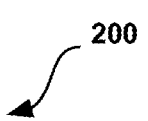
FIG. 3 shows one different example state, s5*a* of a first microtiter plate and two different example states s3*b* and s4*b* of a second microtiter plate in accordance with a second example embodiment 200 of the present disclosure.
Figure 3:
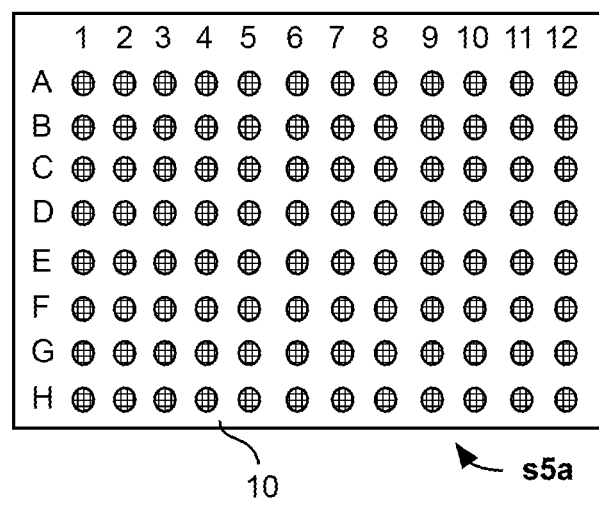
Figure 3:
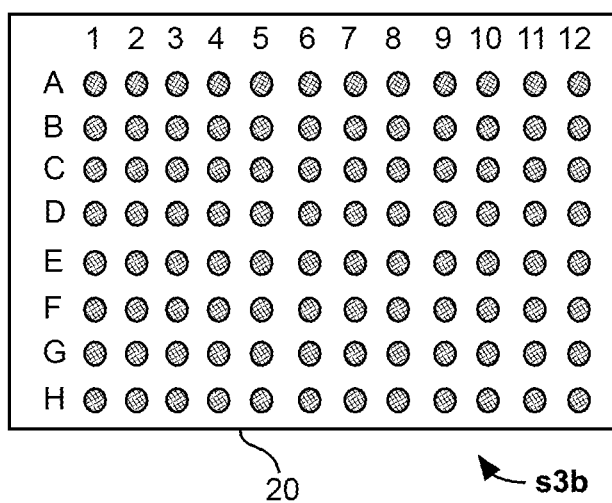
Figure 3:
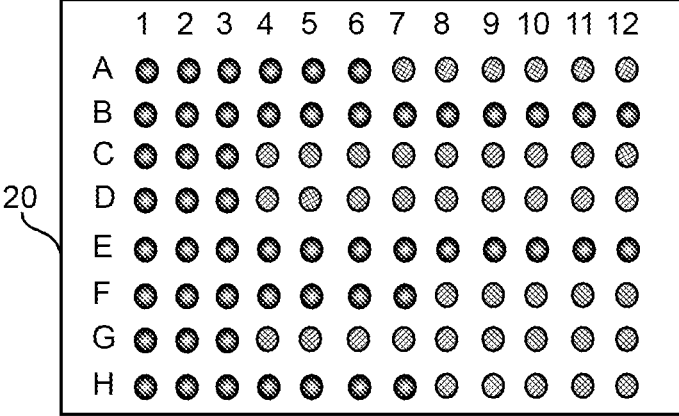

Referring next to FIG. 3, shown therein is one state s5a of a first microtiter plate 10, and two different states, s3b and s4b of a second microtiter plate 20, for the purposes of illustrating a further example embodiment 200 of a method and kit for the identification of an antimicrobial agent and a concentration thereof which can inhibit microbial growth of a microorganism present in a sample fluid.

In order to realize state s5a, initially in an empty microtiter plate 10 such as shown in FIG. 1, a plurality of dilution ranges of a plurality antimicrobial agents is dispensed. In particular, in the wells formed by row A a first dilution range of a first antimicrobial agent is dispensed, in the wells formed by row B a second dilution range of a second antimicrobial agent is dispensed, in the wells formed by row C a third dilution range of a third antimicrobial agent is dispensed, and so on, until a total of 8 dilution ranges of 8 antimicrobial agents is dispensed in row A to H of microtiter plate 10. It is noted that by way of control, no antimicrobial agent is included in wells A1, B1, C1, D1, E1, F1, G1 and H1 of microtiter plate 10. Similar to example embodiment 100, each of the ranges of antimicrobial agents is dispensed from a low concentration of antimicrobial agent in the wells in column 1 and gradually increasing to a higher concentration in the wells in column 12. In other embodiments, each of the ranges of antimicrobial agents can be dispensed from a high concentration of antimicrobial agent in the wells in column 1 and gradually decreasing to a lower concentration in the wells in column 12. In the shown state s5a, in addition to a plurality of dilution ranges of a plurality antimicrobial agents, the wells of microtiter plate 10 contain microbial growth medium and bacteriophage. Thus, it will be clear that state s5a shown in FIG. 3 corresponds with state s5a shown in FIG. 2A with respect to example embodiment 100, and in state s5a plate 10 shown in FIG. 3 therefore may be used by a user wishing to test a fluid sample comprising microbial cells.

A fluid sample containing microbial cells is then dispensed in all of wells A1-H12 of microtiter plate 10, to form assay mixtures therein and microtiter plate 10 is then incubated under conditions that allow for growth of the microbial cells and the proliferation and production of progeny bacteriophage in the growth medium present in wells A1-H12.

Second microtiter plate 20 contains primary anti-bacteriophage antibodies in all of wells A1-H12. Upon completion of incubation of microtiter plate 10, the assay mixtures are transferred to microtiter plate 20. In particular, assay mixtures are transferred from the wells in microtiter plate 10 to the corresponding wells in microtiter plate 20, i.e., assay mixture from well A1 of microtiter plate 10 is transferred to well A1 of microtiter plate 20, assay mixture from well A2 of microtiter plate 10 is transferred to well A2 of microtiter plate 20, assay mixture from well A3 of microtiter plate 10 is transferred to well A3 of microtiter plate 20, and so on, ensuring that all assay mixtures in A1-H12 in microtiter plate 10 are transferred to corresponding wells A1-H12 in microtiter plate 20. Assay mixtures comprising progeny bacteriophage bind to the primary anti-bacteriophage antibodies present in wells A1-H12 of microtiter plate 20, and upon binding form a primary antibody-bacteriophage complex in wells A1-A12. At second state s3b, primary antibody-bacteriophage complex have been formed in wells A1-A12 in microtiter plate 20. It is noted that that state s3b shown in FIG. 3 corresponds with state s3b shown in FIG. 2B with respect to example embodiment 100.

Continuing to refer to FIG. 3 at fourth state s4b, secondary anti-bacteriophage antibody labeled with a detectable label has been dispensed in each of wells A1-H12 of microtiter plate 20. The labeled secondary anti-bacteriophage antibodies bind to bacteriophage present in wells A1-H12 of microtiter plate 20, and upon binding form a labeled primary antibody-bacteriophage-secondary antibody complex in wells A1-H12 containing progeny bacteriophage. The secondary anti-bacteriophage antibodies are then detected by detecting labeled antibody. In state s4b labeled antibody is detected in wells A1-A6, B1-B12, C1-C3, D1-D3, E1-E12, F1-F7, G1-G3 and H1-H7. No labeled antibody is detected in any other wells. Thus, bacteriophage is present in wells in A1-A6, B1-B12, C1-C3, D1-D3, E1 E12, F1-F7, G1-G3 and H1-H7. Furthermore, bacterial cells therefore were present in corresponding wells A1-A6, B1-B12, C1-C3, D1-D3, E1-E12, F1-F7, G1-G3 and H1-H7 of microtiter plate 10, and, thus, the specific known concentrations of antimicrobial agent present in wells A1-A6, B1-B12, C1-C3, D1-D3, E1-E12, F1-F7, G1-G3 and H1-H7 was insufficient to inhibit bacterial growth. By contrast, in the other wells no bacteriophage is present. Furthermore no bacterial cells therefore were present in the corresponding other wells of microtiter plate 10, and, thus, the specific known concentrations of antimicrobial agent present in the other wells was sufficient to inhibit bacterial growth. Thus, for example, the first antimicrobial agent in row A is able to inhibit bacterial growth at the concentrations of antimicrobial agent included in wells A7-A12, and the seventh antimicrobial agent in row G is able to inhibit bacterial growth at the concentrations of antimicrobial agent included in wells G4-G12. The second and fifth antimicrobial agent in rows B and E, respectively, are unable to inhibit microbial growth at all concentrations tested. It is noted that since wells A1, B1, C1, D1, E1, F1, G1 and H1 were used as a control, not including any antimicrobial agent, a signal is detected in all of these wells, at the same time confirming the presence of a phage-susceptible microorganism in the sample fluid. Thus, from the foregoing results, it is possible to select the first antimicrobial agent having a concentration of at least the known concentration of antimicrobial agent in well A7, the third antimicrobial agent having a concentration of at least the known concentration of antimicrobial agent in well C4, the fourth antimicrobial agent having a concentration of at least the known concentration of antimicrobial agent in well D4, the sixth antimicrobial agent having a concentration of at least the known concentration of antimicrobial agent in well F8, the seventh antimicrobial agent having a concentration of at least the known concentration of antimicrobial agent in well G4, and the eighth antimicrobial agent having a concentration of at least the known concentration of antimicrobial agent in well H8, for inhibition of microbial growth The antimicrobial agents present row B and row E are unable to inhibit microbial growth at all tested concentrations of antimicrobial agent in the range.

Figure 4:
FIG. 4 shows one different example state, s5*a* of a first microtiter plate and two different example states s3*b* and s4*b* of a second microtiter plate in accordance with a third example embodiment 300 of the present disclosure.
Figure 4:
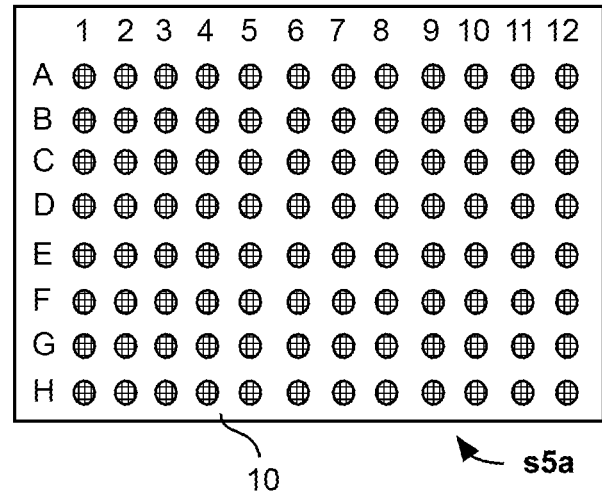
Figure 4:
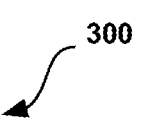
Figure 4:
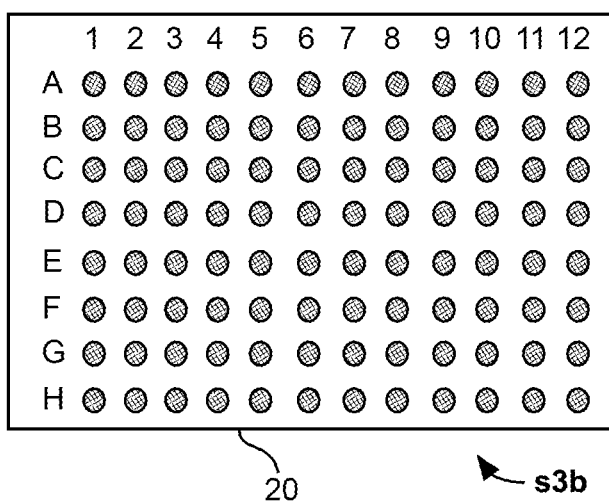
Figure 4:
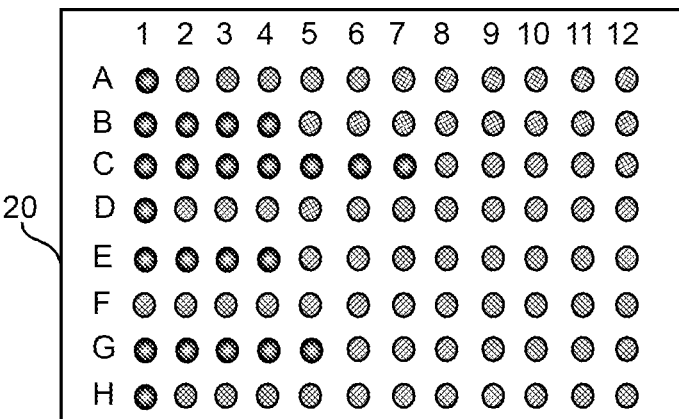

Referring next to FIG. 4, shown therein are a state s5a of a first microtiter plate 10, and two different states, s3b and s4b of a second microtiter plate 20 for the purposes of illustrating a further example embodiment 300 of a method and kit for the identification of an antimicrobial agent and a concentration thereof which can inhibit microbial growth of a microorganism present in a sample fluid.

In order to realize state s5a, microtiter plate 10 has been assembled to dispense therein a plurality of dilution ranges of a single antimicrobial agent. In particular, in the wells of row A of microtiter plate 10 a first dilution range of a an antimicrobial agent has been dispensed, in the wells of row B the same dilution range of the same antimicrobial agent has been dispensed, in the wells of row C the same dilution range of the same antimicrobial agent has been dispensed, and so on. Similar to example embodiment 100, each of the ranges has been dispensed from a low concentration of antimicrobial agent in the wells in column 1 and gradually increasing to a higher concentration in the wells in column 12. As noted above, in other embodiments, each of the ranges of antimicrobial agents can dispensed from a high concentration of antimicrobial agent in the wells in column 1 and gradually decreasing to a lower concentration in the wells in column 12. Furthermore, in each of the wells of row A, a first bacteriophage known to be capable of specifically infecting a first microbial species has been dispensed, in the wells of row B, a second bacteriophage known to be capable of specifically infecting a second microbial species has been dispensed, in the wells of row C a third bacteriophage known to be capable of infecting a third microbial species has been dispensed, and so on. Thus, it is to be understood that the bacteriophages are each specifically able to infect one bacterial species. For example, the bacteriophage dispensed in row A can a bacteriophage specifically able to infect *Escherichia coli*, the bacteriophage dispensed in row B can be a bacteriophage specifically able to infect *Staphylococcus aureus*. In the shown state s5a, in addition to a plurality of dilution ranges of a plurality antimicrobial agents, all of the wells A1-H12 of microtiter plate 10 contain microbial growth medium. Thus, it will be clear that state s5a shown in FIG. 4 corresponds with state s5a shown in FIG. 2A with respect to example embodiment 100, and in state s5a plate 10 shown in FIG. 4 therefore may be used by a user wishing to test a fluid sample comprising microbial cells.

A fluid sample containing microbial cells is then dispensed in all of the wells A1-H12 of microtiter plate 10 to form assay mixtures therein and microtiter plate 10 is then incubated under conditions that allow for growth of the microbial cells in the growth medium present in wells A1-H12. The fluid sample contains a plurality of microbial species.

Second microtiter plate 20 contains primary anti-bacteriophage antibodies in all of wells A1-H12, wells. It is noted that the primary anti-bacteriophage antibodies are specific to the bacteriophages dispensed in each of rows A-H. Thus each row contains different primary anti-bacteriophage antibodies. Upon completion of incubation of microtiter plate 10, the assay mixtures are transferred to microtiter plate 20. In particular, assay mixtures are transferred from the wells A1-H12 in microtiter plate 10 to the corresponding wells A1-H12 in microtiter plate 20, i.e., assay mixture from well A1 of microtiter plate 10 is transferred to well A1 of microtiter plate 20, assay mixture from well A2 of microtiter plate 10 is transferred to well A2 of microtiter plate 20, assay mixture from well A3 of microtiter plate 10 is transferred to well A3 of microtiter plate 20, and so on, ensuring that all assay mixtures in A1-H12 in microtiter plate 10 are transferred to wells A1-H12 in microtiter plate 20. Assay mixtures comprising bacteriophage bind to the primary anti-bacteriophage antibodies present in wells A1-H12 comprising bacteriophage of microtiter plate 20, and upon binding form a primary antibody-bacteriophage complex. At second state s3b, primary antibody-bacteriophage complex have been formed in such of wells A1-A12 that contain bacteriophage.

Continuing to refer to FIG. 4 at fourth state s4b, secondary anti-bacteriophage antibody labeled with a detectable label has been dispensed in each of wells A1-H12 of microtiter plate 20. As is the case with the primary anti-bacteriophage antibodies, the labeled secondary bacteriophages dispensed in each of rows A-H are specific to the bacteriophage. Thus, each row contains different labeled secondary anti-bacteriophage antibodies. Assay mixtures comprising bacteriophage bind to the secondary anti-bacteriophage antibodies present in wells A1-H12 of microtiter plate 20, and upon binding form a labeled primary antibody-bacteriophage-secondary antibody complex in wells A1-H12 containing bacteriophage. The labeled secondary anti-bacteriophage antibodies are then detected. Labeled antibody is detected in wells A1, B1-B4, C1-C7, D1, E1-E4, F1, G1-G5 and H1. No labeled antibody is detected in any other wells. Thus, bacteriophage is present in wells A1, B1-B4, C1-C7, D1, E1-E4, F1, G1-G5 and H1. Furthermore bacterial cells therefore were present in wells A1, B1-B4, C1-C7, D1, E1-E4, F1, G1-G5 and H1 of microtiter plate 10, and, thus, the specific known concentrations of antimicrobial agent present in wells in microtiter plate 10 in A1, B1-B4, C1-C7, D1, E1-E4, F1, G1-G5 and H1 was insufficient to inhibit bacterial growth. By contrast, in the other wells no bacteriophage is present. Furthermore, no bacterial cells therefore were present in the corresponding wells of microtiter plate 10, and, thus, the specific known concentrations of antimicrobial agent present in the other wells was sufficient to inhibit bacterial growth. Thus, for example, microbial growth in rows A, D, and H is inhibited by the antimicrobial agent at all concentrations. Thus, the bacterial species known to be specifically infected by the bacteriophages used to prepare rows A, D, and H is present in the fluid sample, and the antimicrobial agent is effective at all concentrations in the range. The bacterial species known to be specifically infected by the bacteriophages used to prepare rows B, is present in the fluid sample, and the antimicrobial agent is effective at a concentration of antimicrobial of at least the concentration included in well B5 in microtiter plate 10. The bacterial species known to be specifically infected by the bacteriophages used to prepare rows C, is present in the fluid sample, and the antimicrobial agent is effective at a concentration of antimicrobial of at least the concentration included in well C8 in microtiter plate 10. The bacterial species known to be specifically infected by the bacteriophages used to prepare rows E, is present in the fluid sample, and the antimicrobial agent is effective at a concentration of antimicrobial of at least the concentration included in well E5 in microtiter plate 10. The bacterial species known to be specifically infected by the bacteriophages used to prepare rows G, is present in the fluid sample, and the antimicrobial agent is effective at a concentration of antimicrobial of at least the concentration included in well G6 in microtiter plate 10. It is noted that wells A1, B1, C1, D1, E1, F1, G1 and H1 were used as a control, not including any antimicrobial agent. In wells A1, B1, C1, D1, E1, G1 and H1 a signal is detected. No signal is detected in well F1. The detected signal indicates the presence of each of the microbial species in the fluid sample of each of the bacterial species for which a specific bacteriophage was included in rows A, B, C, D, E, G and H of microtiter plate 10. The absence of a signal in well F1 indicates the absence in the fluid sample of the bacterial species for which a specific bacteriophage was included in row F, since even in the absence of antimicrobial agent, no signal is detected.

Furthermore, it should be understood that since the microbial specificity of the bacteriophage dispensed in each row of microtiter plate 10 is known, the fluid sample can be confirmed to contain a specific microbial species if a signal is detected in at least the control wells A1, B1, C1, D1, E1, F1, G1 or H1. Thus, if the bacteriophage dispensed in row A of microtiter plate 10 is a bacteriophage specifically able to infect *Escherichia coli*, and the bacteriophage dispensed in row B of microtiter plate 10 is a bacteriophage specifically able to infect *Staphylococcus aureus*, the detection of a signal in at least well A1 and well B1 of microtiter plate 20 indicates the presence of both *Escherichia coli* and *Staphylococcus aureus* in the fluid sample. If for, example, the bacteriophage dispensed in row F of microtiter plate 10 is a bacteriophage specifically able to infect *Klebsiella pneumoniae* and no signal is detected in at least well F1 of microtiter plate 20, this indicates *Klebsiella pneumoniae* is absent in the fluid sample. Thus, it can now be appreciated that in accordance, with an aspect, and an embodiment hereof, in the performance of a single diagnostic test, the microbial species in a fluid sample may be identified, and a suitable antimicrobial agent to inhibit growth thereof, and a suitable concentration of the antimicrobial agent. Thus, the methods of the present disclosure can limit the time from having acquired a fluid sample suspected to contain a microbial organisms, to the time of identifying the microbial species, a suitable antimicrobial agent and a suitable concentration.

Figure 5:
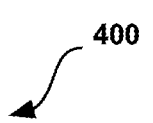
FIG. 5 shows one different example state, s5*a* of a first microtiter plate and two different example states s3*b* and s4*b* of a second microtiter plate in accordance with a fourth example embodiment 400 of the present disclosure.
Figure 5:
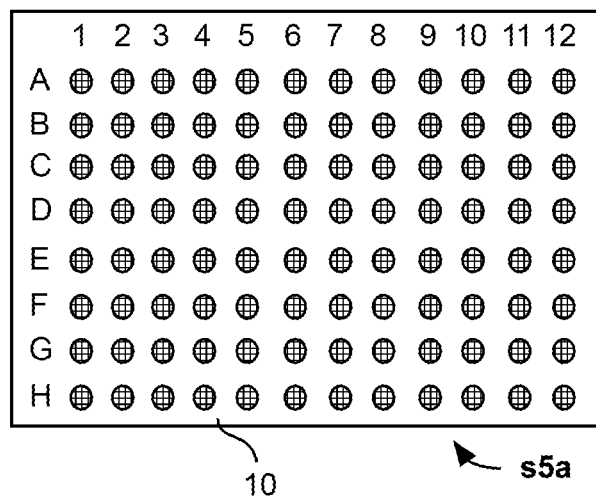
Figure 5:
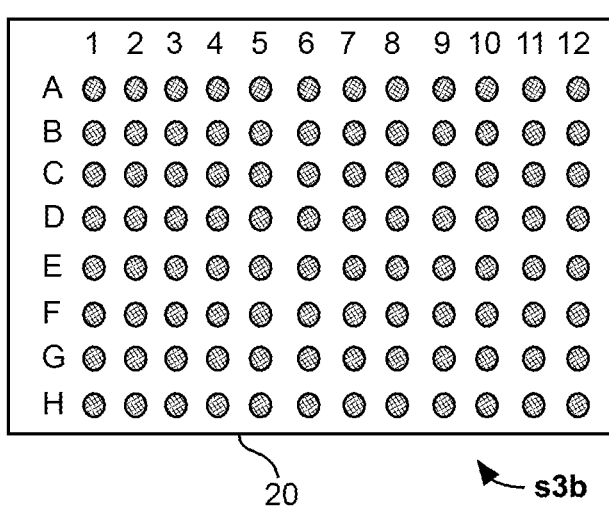

Referring next to FIG. 5, shown therein are three different states s5a of a first microtiter plate 10, and two different states, s3b and s4b of a second microtiter plate 20 for the purposes of illustrating a further example embodiment 400 of a method and kit for the identification of an antimicrobial agent and a concentration thereof which can inhibit microbial growth of a microorganism present in a sample fluid.

In order to realize state s5a, microtiter plate 10 has been assembled to dispense therein a plurality of dilution ranges of a single antimicrobial agent. In particular, in the wells of row A a first dilution range of a first antimicrobial agent has been dispensed, in the wells of row B the same dilution range of a second antimicrobial agent has been dispensed, in the wells of row C a same dilution range of a third antimicrobial agent has been dispensed, and so on. Similar to example embodiment 100, each of the ranges has been dispensed from a low concentration of antimicrobial agent in the wells in column 1 and gradually increasing to a higher concentration in the wells in column 12. As noted above, in other embodiments, each of the ranges of antimicrobial agents can dispensed from a high concentration of antimicrobial agent in the wells in column 1 and gradually decreasing to a lower concentration in the wells in column 12. Furthermore, in each of the wells of row A a plurality of bacteriophages, for example, a mixture of 2, 3, 4, 5, 6, or more bacteriophages known to be capable of specifically infecting an equal plurality of microbial species has been dispensed. In the wells of row B, the same plurality of bacteriophages has been dispensed. In the wells of row C the same plurality of bacteriophages has been dispensed, and so on. Thus, for example, in the wells of each of the rows A-H, a mixture of 3 bacteriophages known to be capable of infecting *E. coli, K. pneumoniae*, and *S. aureus* may be dispensed In the shown state s5a, in addition to a plurality of dilution ranges of a plurality antimicrobial agents, and bacteriophage, bacterial growth medium has been dispensed in the wells A1-H12 of microtiter plate 10. Thus, it will be clear that state s5a shown in FIG. 5 corresponds with state s5a shown in FIG. 2A with respect to example embodiment 100, and in state s5a plate 10 shown in FIG. 5 therefore may be used by a user wishing to test a fluid sample comprising microbial cells.

A fluid sample containing a mixture of microbial cells is then dispensed in all of the wells of microtiter plate 10, to form assay mixtures therein and microtiter plate 10 is then incubated under conditions that allow for growth of the microbial cells in the growth medium present in wells A1-H12.

Continuing to refer to FIG. 5, second microtiter plate 20 contains primary anti-bacteriophage antibodies in all of wells A1-H12. It is noted that the primary anti-bacteriophage antibodies are a mixture of primary anti-bacteriophage antibodies, capable of binding to each of the bacteriophages in the plurality of bacteriophages included in the wells of microtiter plate 10. Thus, if, for example, three different bacteriophages were included in the wells of microtiter plate 10, the primary anti-bacteriophage antibodies are a mixture of three antibodies, each able to bind to one of the three bacteriophages, for example, a primary antibody capable of binding an *E. coli* bacteriophage, a primary antibody capable of binding a *K. pneumoniae* bacteriophage, and a primary antibody capable of binding an *S. aureus* bacteriophage. Upon completion of incubation of microtiter plate 10, the assay mixtures are transferred to microtiter plate 20. In particular, assay mixtures are transferred from the wells in microtiter plate 10 to the corresponding wells in microtiter plate 20, i.e., assay mixture from well A1 of microtiter plate 10 is transferred to well A1 of microtiter plate 20, assay mixture from well A2 of microtiter plate 10 is transferred to well A2 of microtiter plate 20, assay mixture from well A3 of microtiter plate 10 is transferred to well A3 of microtiter plate 20, and so on, ensuring that all assay mixtures in A1-H12 in microtiter plate 10 are transferred to wells A1-H12 in microtiter plate 20. Assay mixtures comprising bacteriophage will bind to the primary anti-bacteriophage antibodies present in wells A1-H12 comprising bacteriophage of microtiter plate 20, and upon binding form a primary antibody-bacteriophage complex in wells A1-H12. At second state s4*b*, primary antibody-bacteriophage complex have been formed in wells A1-H12.

Continuing to refer to FIG. 5 at fourth state s4*b*, secondary anti-bacteriophage antibody labeled with a detectable label have been dispensed in each of wells A1-H12 of microtiter plate 20. Assay mixtures comprising bacteriophage bind to the secondary anti-bacteriophage antibodies present in wells A1-H12 of microtiter plate 20, and upon binding form a labeled primary antibody-bacteriophage-secondary antibody complex in wells A1-H12 containing bacteriophage. The secondary anti-bacteriophage antibodies are detected in wells A1-A5, B1-B12, C1-C12, D1-D12, E1-E3, F1-F12, G1-G7 and H1-H12. No labeled antibody is detected in any other wells. Thus, bacteriophage is present in wells A1-A5, B1-B12, C1-C12, D1-D12, E1-E3, F1-F12, G1-G7 and H1-H12. Furthermore bacterial cells therefore were present in wells in corresponding wells A1-A5, B1-B12, C1-C12, D1-D12, E1-E3, F1-F12, G1-G7 and H1-H12 of microtiter plate 10, and thus the specific known concentrations of antimicrobial agent present in wells A1-A5, B1-B12, C1-C12, D1-D12, E1-E3, F1-F12, G1-G7 and H1-H12 was insufficient to inhibit bacterial growth. By contrast, in the other wells no bacteriophage is present. Furthermore, therefore, no bacterial cells were present in the corresponding wells of microtiter plate 10, and, thus, the specific known concentrations of antimicrobial agent present in the other wells was sufficient to inhibit bacterial growth. Thus, for example, the antimicrobial agents in rows B, C, D, F and H are unable to inhibit bacterial growth of the microbial species present in the fluid sample, at the concentrations of antimicrobial agent included in the wells in these rows. Thus, these antimicrobial agents are unlikely to be suitable for use. On the other hand, the antimicrobial agents present in rows A, E and G are able to inhibit microbial growth at concentrations of antimicrobial agent of at least the concentrations present in wells A6, E4 and G8, respectively, and thus these antimicrobial agents may be used at least at these concentrations to inhibit growth of the known microbial species. Thus, for example, if a mixture of three bacteriophages known to be capable of infecting *E. coli, K. pneumoniae*, and *S. aureus* was used, and the sample contained at least one of *E. coli, K. pneumoniae*, and *S. aureus*, the antimicrobial agents present in rows A, E and G would likely be effective to control proliferation of the least one of *E. coli, K. pneumoniae*, and *S. aureus*. Thus, if one or two or three of these species were present in the sample, the antimicrobial agents present in A, E and G were likely effective to control growth thereof. It is noted however that the performance of this embodiment does not allow for the distinction of the bacterial species is present in the sample, e.g., it is not possible to determine if *E. coli, K. pneumoniae*, and *S. aureus* are present in the sample. Instead, it is merely possible to ascertain that at least one of these species is present. If desired, a further assay assembled in accordance with embodiment 300 may be assembled to identify which individual species is present. It is noted that since wells A1, B1, C1, D1, E1, F1, G1 and H1 were used as a control not including any antimicrobial agent, and since the sample contained at least one of the microbial species present in the sample (e.g., least one of *E. coli, K. pneumoniae*, and *S. aureus*), a signal is detected in all of these wells.

As can now be appreciated from the foregoing example embodiments 100, 200, 300 and 400, that the present disclosure includes various methods for determining an effective concentration of an antimicrobial agent for inhibiting bacterial growth, including, in one aspect, in an embodiment, a method for determining of an effective concentration of an antimicrobial agent for inhibiting bacterial growth, the method comprising:

a) transferring a sample of living microbial cells to a first plurality of wells of a first microtiter plate, the first plurality of wells containing a range of known concentrations of at least one antimicrobial agent, each well of the first plurality of wells further containing bacterial growth medium and bacteriophage capable of infecting the microbial cells, to thereby form assay mixtures in each of the first plurality of wells;

b) incubating the first microtiter plate under conditions sufficient to promote bacterial growth and infection of the bacterial cells by the bacteriophage, and cause the production of progeny bacteriophage in the assay mixtures;

c) transferring the assay mixtures from the first plurality of wells of the first microtiter plate to a corresponding second plurality of wells of a second microtiter plate, each of the second plurality of wells containing primary anti-bacteriophage antibodies to thereby bind the progeny bacteriophage to the primary antibodies and form a primary antibody-bacteriophage complex; and d) detecting the primary antibody-bacteriophage complex in the second plurality of wells, wherein an effective concentration of the antimicrobial agent is a known concentration in one or more wells in the first plurality of wells that corresponds with one or more wells in the second plurality of wells in which the primary antibody-bacteriophage complex is not detected.

In one embodiment, the primary antibody is labeled with a detectable label, and the detecting comprises: detecting the labeled primary antibody-bacteriophage-complex in the second plurality of wells, wherein an effective concentration of the antimicrobial agent is a known concentration in one or more wells in the first plurality of wells that corresponds with one or more wells in the second plurality of wells in which substantially no labeled primary antibody-bacteriophage complex is detected.

In one embodiment, the detecting comprises:

contacting the primary antibody-bacteriophage complex with a secondary anti-bacteriophage antibody labeled with a detectable label to thereby bind the primary antibody-bacteriophage complex to the secondary bacteriophage antibody and form a labeled primary antibody-bacteriophage-secondary antibody complex; and detecting the labeled primary antibody-bacteriophage-secondary antibody complex in the second plurality of wells, wherein an effective concentration of the anti-microbial agent is a known concentration in one or more wells in the first plurality of wells that corresponds with one or more wells in the second plurality of wells in which substantially no labeled primary antibody-bacteriophage-secondary antibody complex is detected.

Furthermore, in an aspect, the methods of the present disclosure may be carried out using an assembly of materials and compositions in the form of a kit, the kit further including instructions for use thereof. The instructions may be included with the kit (e.g., printed on paper and provided directly with the kit), and/or a reference may be provided for on-line access (e.g., on a desktop computer, laptop computer, tablet or mobile phone) to the instructions, all of which are intended to be included herein. The instructions may additionally comprise further information regarding the products and its use, e.g., safety information. Accordingly, the present disclosure further provides, in an aspect, in an embodiment, a kit for determining of an effective concentration of an antimicrobial agent for inhibiting bacterial growth, the kit comprising:

a) first microtiter plate comprising a plurality of wells comprising bacteriophage capable of infecting microbial cells; and b) a second microtiter plate comprising a plurality of wells comprising primary anti-bacteriophage antibodies capable of binding the bacteriophage, together with instructions to determine an effective concentration of an antimicrobial agent for inhibiting bacterial growth by:

(i) transferring a sample of living microbial cells to a first plurality of wells of the first microtiter plate, the first plurality of wells containing a range of known concentrations of at least one antimicrobial agent, each well of the first plurality of wells further containing bacterial growth medium, the bacteriophage in the plurality of wells being capable of infecting the microbial cells, to thereby form assay mixtures in each of the first plurality of wells;

(ii) incubating the first microtiter plate under conditions sufficient to promote bacterial growth and infection of the bacterial cells by the bacteriophage, and cause the production of progeny bacteriophage in the assay mixtures;

(iii) transferring the assay mixtures from the first plurality of wells of the first microtiter plate to a corresponding second plurality of wells of the second microtiter to thereby bind the progeny bacteriophage to the primary anti-bacteriophage antibodies and form a primary antibody-bacteriophage complex; and (iv) detecting the primary antibody-bacteriophage complex.

In one embodiment, the primary antibody is labeled with a detectable label, and the detecting comprises:

detecting the labeled primary antibody-bacteriophage-complex in the second plurality of wells, wherein an effective concentration of the antimicrobial agent is a known concentration in one or more wells in the first plurality of wells that corresponds with one or more wells in the second plurality of wells in which substantially no labeled primary antibody-bacteriophage complex is detected.

In one embodiment the detecting comprises:

contacting the primary antibody-bacteriophage complex with a secondary anti-bacteriophage antibody labeled with a detectable label to thereby bind the primary antibody-bacteriophage complex to the secondary bacteriophage antibody and form a labeled primary antibody-bacteriophage-secondary antibody complex; and detecting the labeled primary antibody-bacteriophage-secondary antibody complex in the second plurality of wells, wherein an effective concentration of the antimicrobial agent is a known concentration in one or more wells in the first plurality of wells that corresponds with one or more wells in the second plurality of wells in which substantially no labeled primary antibody-bacteriophage-secondary antibody complex is detected.

It is noted that in use of the kits different steps may be carried out at different locations. Thus, for example, step (i) and (ii) may be carried out at a first location, for example, a site at which the fluid sample is collected. The first microtiter plate may following incubation be transferred to another site, for example a diagnostic laboratory, for the performance of steps (iii), (iv) and (v). This may, for example, be desirable when at the first site, e.g., the sample collection site, the compositions necessary to conduct steps (iii), (iv) and (v) are not available and/or the conditions to conduct steps (iii), (iv) and (v) are not suitable. Following initial sample collection, the first microtiter plate may be then be shipped to a location, such as a diagnostic laboratory, more suitable for further processing, notably the performance of steps (iii), (iv) and (v).

In another aspect, the present disclosure provides, in at least one aspect, in at least one embodiment, an assembly of reagents for use in conjunction with a kit or the methods of the present disclosure. The reagent assembly includes at least bacteriophage and anti-bacteriophage antibodies in quantities sufficient for suspension in a first and second microtiter plate. The reagent assembly may further optionally include, one or more of the following: bacterial cells, secondary anti-bacteriophage antibody, an anti-microbial agent, bacterial growth medium and a diluent.

Of course, the above described example embodiments of the present disclosure are intended to be illustrative only and in no way limiting. The described embodiments are susceptible to many modifications of composition, details and order of operation. Various embodiments of the disclosure, rather, are intended to encompass all such modifications within its scope, as defined by the claims, which should be given a broad interpretation consistent with the description as a whole.

Hereinafter are provided examples of specific embodiments and implementations for performing the methods of the present disclosure, as well as implementations representing the systems or kits of the present disclosure. The examples are provided for illustrative purposes only, and are not intended to limit the scope of the present disclosure in any way.

EXAMPLES

Example 1—Minimum Inhibitory Concentration Determination of Select Carbapenem and β-Lactam Antimicrobials by Serial Microdilution Against MDR *E. coli* in Urine Samples The method was performed with phage amplification by addition of one each of four carbapenems (Imipenem, Meropenem, Doripenem, or Ertapenem) or one each of four β-lactams (Oxacillin, Ceftazidime, Ceftriaxone or Cefepime) to successive wells of a 96-well microtiter plate (also referred to as a "reaction plate") followed by addition of 100 uL of a liquid suspension each of a single ATCC *E. coli* strain per reaction, using the *E. coli* strains shown in Table 1. These ATCC strains were normalized to a concentration of ~1×10^6 cfu/mL (this is the average bacterial concentration associated with symptomatic UTI) and were prepared in urine specimens collected from healthy volunteers. Each antimicrobial was assayed individually by broth microdilution in eight to twelve two- or 10-fold serial dilutions, depending on the drug, in a range from 0.5 to 256 ug/mL, as established by the Clinical and Laboratory Standards Institute (Performance Standards for Antimicrobial Susceptibility Testing. 32^{nd} Edition. CLSI Supplement M100, Clinical and Laboratory Standards Institute, 2022). Dilutions of antimicrobials were performed in diluent according to the CLSI reference and the diluted antimicrobials were added to a single column of wells in the reaction plate. In this way, in each of a total of 9 plates (each plate including samples containing a different *E. coli* strain), a column of wells received a single antimicrobial that was serially diluted from high concentration (bottom of reaction plate (or row "H") in FIG. 6) to low concentration (top of reaction plate (or row "B" in FIG. 6). The top row of wells (row "A") of the reaction plate in FIG. 6 are blanks containing sample diluent only. Thus, the highest concentration of antimicrobial starts in row H of the reaction plate and the concentration of antimicrobial agent decreases as one proceeds upwards along the rows of the reaction plate towards row B. *E. coli*-specific phage T7 (ATCC BAA-1025-B2) was next added to the wells at a multiplicity of infection (MOI) of ~0.5 or 1×10^3 pfu/mL (below assay limits of detection). Amplification reactions were allowed to proceed for 2 hours at 37° C. and then assayed by transfer of 100 uL of each reaction at each drug concentration to a second microtiter plate containing a second plurality of corresponding wells (referred to as the "detection plate") pre-coated with anti-phage capture antibody (referred to as the "detection plate") Bethyl Labs polyclonal anti-T7 (part A190-117A)) on which ELISA was then performed. The ELISA methodology is described below.

Two ELISA plates were used, the first for phages diluted to 10 µg/mL in carbonate/bicarbonate buffer, the second for phages diluted to 10 µg/mL in urine. The ELISA detection plates were prepared by applying a direct passive coating of anti-T7 capture antibody at a concentration of 10 µg/ml prior to assays. After this preparation, a conventional ELISA protocol was followed:

1. 100 µl/well of each phage reaction from the reaction plate was added and incubated at room temperature for 1 hr, with blanks. The blanks were the first row of wells each of carbonate/bicarbonate buffer diluent only.
2. Plates were inverted and shaken on a paper towel to remove residual liquid.
3. Plates were blocked with 300 µL blocking buffer, sealed with adhesive film covering, and incubated at 4° C. overnight.
4. Plates were inverted.
5. Primary antibody was added at corresponding dilutions to wells at 100 µl/well and incubated at room temperature for 1 hr.
6. Plates were washed 4 time with an automated plate washer.
7. Secondary biotinylated anti-T7 antibody was diluted from stock at 1/30,000 in PBS; 100 µL/well was added; incubated at room temperature for 30 min.
8. Plates were washed 4 times.
9. Streptavidin conjugated TMB was added, incubated at room temperature for 30 min.
10. Plates were washed 4 time.
11. TMB substrate was added, 100 µL/well and incubated in the dark for 10 min at room temperature.
12. The reaction was stopped with Stop Solution (0.36N $H_2SO_4$) by pipetting 100 µL/well.
13. Absorbance readings were taken on plate reader at 450 nm, data was exported to a spreadsheet and saved.

A photographic image showing a representative reaction plate (left) and a detection plate (right) is shown in FIG. 6.

If the target bacteria were resistant at any of the given drug concentrations and were thus viable, a corresponding increase of progeny phage concentration above the ~1×10^3 pfu/mL detection threshold resulted in production of a detectable phage-amplified colorimetric ELISA signal (see e.g., wells B3, B4, B7, B8) and thus indicated a given MIC based on the known drug concentration. If the target bacteria were susceptible at a given drug concentration, cells were rendered non-viable and thus precluded phage amplification (see e.g., wells H3, H4, H7, H8), prohibiting signal production. In this binary fashion, CLSI-published MIC values were then consulted to determine organism resistance, susceptibility or intermediate susceptibility based on drug concentration, with MIC determined by whether phage amplification occurred or not. The foregoing was repeated using samples containing the additional *E. coli* strains noted in Table 1. Results are summarized shown in Table 1.

TABLE 1

| | *E. coli* MDR strains in urine | | | | | | | | |
|---|---|---|---|---|---|---|---|---|---|
| | BAA 196 | BAA 197 | BAA 198 | BAA 2340 | BAA 2452 | BAA 2471 | BAA 2523 | O157: H7 | 15597 |
| Carbapenems | MIC (ug/ml) | | | | | | | | |
| Imipenem | 16 | 32 | 64 | >64 | 256 | 32 | 64 | 64 | 4 |
| Meropenem | 16 | 64 | 16 | 16 | 16 | 16 | 1 | 0.25 | >64 |
| Doripenem | 16 | 32 | 32 | 16 | 16 | 256 | 0.5 | 0.25 | >64 |
| Ertapenem | 64 | >64 | 64 | 68 | 16 | >256 | 8 | 2 | 0.5 |
| β-lactams | | | | | | | | | |
| Oxacillin | >64 | >64 | >64 | >64 | 64 | >256 | 256 | >256 | 64 |
| Ceftazidime | >64 | >64 | >64 | >64 | 16 | >256 | >256 | 256 | 0.5 |
| Ceftriaxone | >64 | >64 | >64 | >64 | 68 | >256 | 256 | 64 | 8 |
| Cefepime | 64 | >64 | 64 | 68 | 68 | >256 | 16 | 8 | 8 |

The invention claimed is:

1. A method for determining an effective concentration of an antimicrobial agent for inhibiting bacterial growth, the method comprising:
   a) transferring a sample containing living bacterial cells to a first plurality of wells of a first multiwell receptacle, the first plurality of wells containing a range of known concentrations of at least one antimicrobial agent, each well of the first plurality of wells further containing bacterial growth medium and bacteriophage capable of infecting the bacterial cells, to thereby form assay mixtures in each well of the first plurality of wells, wherein the bacteriophage is present at a concentration that is sufficiently low to not be detectable in step d);
   b) incubating the first multiwell receptacle under conditions sufficient to promote bacterial growth and infection of the bacterial cells by the bacteriophage, and cause the production of progeny bacteriophage in the assay mixtures;
   c) transferring the assay mixtures from the first plurality of wells of the first multiwell receptacle to a corresponding second plurality of wells of a second multiwell receptacle, each of the corresponding wells of the second plurality of wells containing primary anti-bacteriophage antibodies to thereby bind the progeny bacteriophage to the primary antibodies and form a primary antibody-bacteriophage complex; and
   d) detecting the primary antibody-bacteriophage complex in the corresponding second plurality of wells of the second multiwell receptacle, to thereby determine an effective concentration of the antimicrobial agent, wherein an effective concentration of the antimicrobial agent is a known concentration in one or more wells in the first plurality of wells that corresponds with one or more wells in the second plurality of wells in which the primary antibody-bacteriophage complex is not detected.

2. A method according to claim 1, wherein the primary antibody is labeled with a detectable label, and the detecting comprises: detecting the labeled primary antibody-bacteriophage-complex in the second plurality of wells, wherein an effective concentration of the antimicrobial agent is a known concentration in one or more wells in the first plurality of wells that corresponds with one or more wells in the second plurality of wells in which substantially no labeled primary antibody-bacteriophage complex is detected.

3. A method according to claim 1, wherein the detecting comprises:
   contacting the primary antibody-bacteriophage complex with a secondary anti-bacteriophage antibody labeled with a detectable label to thereby bind the primary antibody-bacteriophage complex to the secondary bacteriophage antibody and form a labeled primary antibody-bacteriophage-secondary antibody complex; and
   detecting the labeled primary antibody-bacteriophage-secondary antibody complex in the second plurality of wells, wherein an effective concentration of the antimicrobial agent is a known concentration in one or more wells in the first plurality of wells that corresponds with one or more wells in the second plurality of wells in which substantially no labeled primary antibody-bacteriophage-secondary antibody complex is detected.

4. A method according to claim 1, wherein the first multiwell receptacle contains a control assay mixture including the bacterial growth medium and the bacteriophage, the control assay mixture not containing antimicrobial agent.

5. A method according to claim 4, wherein the control assay mixture includes a control sample known to contain the living bacterial cells.

6. A method according to claim 1, wherein the range of known concentrations of antimicrobial agent is distributed along a row or column of wells in the first multiwell receptacle.

7. A method according to claim 6, wherein the range of known concentrations includes at least three different known concentrations distributed along the row or column from highest to lowest concentration.

8. A method according to claim 1, wherein the range of known concentrations of antimicrobial agent is a serial dilution containing at least three different concentrations.

9. A method according to claim 8, wherein the serial dilution is distributed along a row or column of wells in the first multiwell receptacle from highest to lowest concentration.

10. A method according to claim 1, wherein the multiwell receptacle contains a plurality of ranges of known concentrations of a corresponding plurality of antimicrobial agents.

11. A method according to claim 10, wherein each of the ranges of the plurality of ranges is distributed along a different column or row of wells of the first multiwell receptacle.

12. A method according to claim 10, wherein each of the ranges of the plurality of ranges is distributed along a different column or row of wells of the first multiwell receptacle, each range including at least three different known concentrations, each concentration in the range distributed along the wells of a column or row from highest to lowest concentration.

13. A method according to claim 1, wherein the sample containing living bacterial cells is a sample containing bacterial cells of two or more bacterial species, and the first multiwell receptacle contains bacteriophage capable of producing progeny in the two or more bacterial species.

14. A method according to claim 1, wherein the sample containing living bacterial cells is a sample containing bacterial cells of two or more bacterial species, and the first multiwell receptacle contains two or more bacteriophage strains, each bacteriophage strain capable of producing progeny in a single species of the two or more bacterial species.

15. A method according to claim 14, wherein the two or more bacteriophage strains capable of producing progeny in the two or more bacterial species are each contained in separate wells.

16. A method according to claim 15, wherein each bacteriophage strain of the two or more bacteriophage strains is distributed along a different row or column of the first multiwell receptacle, each row or column further containing a range of concentrations of the same antimicrobial agent, each range including at least three different known concentrations of the antimicrobial agent, distributed along each row or column from highest to lowest concentration.

17. A method according to claim 14, wherein the two or more bacteriophage strains capable of producing progeny in the two or more bacterial species are both contained in the same wells to form a mixture of bacteriophage strains in the wells.

18. A method according to claim 17, wherein the mixture of bacteriophage strains is distributed along rows or columns of the first multiwell receptacle, each row or column further containing a range of concentrations of a plurality of antimicrobial agents, each range including at least three different known concentrations of the at least one antimicrobial agent, distributed along each row or column from highest to lowest concentration, the second multiwell receptacle containing in a plurality of wells a mixture of two or more primary anti-bacteriophage antibodies in each well of the plurality of wells, the primary anti-bacteriophage antibodies capable of binding each of the bacteriophage strains.

19. A method according to claim 1, wherein the bacterial cells are human or animal pathogenic bacterial cells.

20. A method according to claim 1, wherein the bacterial cells belong to the group of genera consisting of *Enterococcus, Staphylococcus, Klebsiella, Acinetobacter, Pseudomonas* and *Enterobacter*.

21. A method according to claim 1, wherein the bacterial cells belong to the group of species consisting of *Enterococcus faecium, Staphylococcus aureus, Klebsiella pneumoniae, Acinetobacter baumannii, Pseudomonas aeruginosa* and *Enterobacter cloacae*.

22. A kit for determining an effective concentration of an antimicrobial agent for inhibiting bacterial growth, the kit comprising:

a) a first multiwell receptacle comprising a first plurality of wells comprising bacteriophage capable of infecting bacterial cells in a concentration that is sufficiently low to not be detectable in step (iv); and b) a second multiwell receptacle comprising a corresponding second plurality of wells comprising primary anti-bacteriophage antibodies capable of binding the bacteriophage, together with instructions to determine an effective concentration of an antimicrobial agent for inhibiting bacterial growth by (i) transferring a sample containing living bacterial cells to a first plurality of wells of the first multiwell receptacle, the first plurality of wells containing a range of known concentrations of at least one antimicrobial agent, each well of the first plurality of wells further containing bacterial growth medium, the bacteriophage in the plurality of wells being capable of infecting the bacterial cells, to thereby form assay mixtures in each of the wells of the first plurality of wells;

(ii) incubating the first multiwell receptacle under conditions sufficient to promote bacterial growth and infection of the bacterial cells by the bacteriophage, and cause the production of progeny bacteriophage in the assay mixtures;

(iii) transferring the assay mixtures from the first plurality of wells of the first multiwell receptacle to a corresponding second plurality of wells of the second multiwell receptacle to thereby bind the progeny bacteriophage to the primary anti-bacteriophage antibodies and form a primary antibody-bacteriophage complex; and (iv) detecting the primary antibody-bacteriophage complex to thereby determine an effective concentration of the antimicrobial agent, wherein an effective concentration of the antimicrobial agent is a known concentration in one or more wells in the first plurality of wells that corresponds with one or more wells in the second plurality of wells in which substantially no labeled primary antibody-bacteriophage complex is detected.

* * * * *